(12) United States Patent
Dann et al.

(10) Patent No.: US 10,792,413 B2
(45) Date of Patent: Oct. 6, 2020

(54) IMPLANTABLE AND REMOVABLE CUSTOMIZABLE BODY CONDUIT

(71) Applicant: Merit Medical Systems, Inc., South Jordan, UT (US)

(72) Inventors: Mitchell Dann, Wilson, WY (US); Judson A. Herrig, Elko, MN (US); Stephen Hohmann, Dallas, TX (US)

(73) Assignee: Merit Medical Systems, Inc.

( * ) Notice: Subject to any disclaimer, the term of this patent is extended or adjusted under 35 U.S.C. 154(b) by 45 days.

(21) Appl. No.: 14/192,567

(22) Filed: Feb. 27, 2014

(65) Prior Publication Data
US 2014/0180190 A1   Jun. 26, 2014

Related U.S. Application Data

(60) Division of application No. 13/151,157, filed on Jun. 1, 2011, now abandoned, which is a
(Continued)

(51) Int. Cl.
*A61M 1/36* (2006.01)
*A61F 2/06* (2013.01)
*A61M 25/00* (2006.01)

(52) U.S. Cl.
CPC .......... *A61M 1/3655* (2013.01); *A61F 2/064* (2013.01); *A61F 2250/0059* (2013.01); *A61M 25/005* (2013.01); *A61M 2025/0024* (2013.01)

(58) Field of Classification Search
CPC ........ A61M 1/3655; A61M 2025/0024; A61M 2025/0197; A61M 25/005;
(Continued)

(56) References Cited

U.S. PATENT DOCUMENTS

| 3,357,432 A | 12/1967 | Sparks |
| 3,363,926 A | 1/1968 | Wilson |

(Continued)

FOREIGN PATENT DOCUMENTS

| DE | 4418910 | 12/1995 |
| DE | 29515546 | 3/1997 |

(Continued)

OTHER PUBLICATIONS

Co-pending Reissue U.S. Appl. No. 10/219,998 and its prosecution history.

(Continued)

*Primary Examiner* — Shaun L David
(74) *Attorney, Agent, or Firm* — Stoel Rives LLP

(57) ABSTRACT

An apparatus and method are provided to treat a stenosis. A delivery device is provided that has an elongate tubular member coupled therewith. The elongate tubular member has an outside surface that is configured to prevent adherence of in vivo matter. The tubular member has a proximal end and a distal end and is reinforced along its length to maintain open lumen under a transverse load. The tubular member is placed in the vasculature such that the distal end of the elongate tubular member is disposed distal of a stenosis. The proximal end of the elongate tubular member is disposed inside the vessel, preferably at a location proximal of the stenosis. Thereafter, after a therapeutic period, the elongate tubular member is removed intact.

10 Claims, 12 Drawing Sheets

Related U.S. Application Data continuation-in-part of application No. 12/397,275, filed on Mar. 3, 2009, now Pat. No. 8,079,973.

(60) Provisional application No. 61/034,125, filed on Mar. 5, 2008.

(58) Field of Classification Search
CPC ... A61M 2220/0033; A61F 2/064; A61F 2/95; A61F 2002/9522; A61F 2002/9534; A61F 2002/9528
See application file for complete search history.

(56) References Cited

U.S. PATENT DOCUMENTS

| | | | |
|---|---|---|---|
| 3,435,823 A | 4/1969 | Edwards | |
| 3,490,438 A | 1/1970 | Lavender et al. | |
| 3,683,926 A | 8/1972 | Suzuki | |
| 3,814,137 A | 6/1974 | Martinez | |
| 3,818,511 A | 6/1974 | Goldberg et al. | |
| 3,826,257 A | 7/1974 | Buselmeier | |
| 3,853,126 A | 12/1974 | Schulte | |
| 3,882,862 A | 5/1975 | Berend | |
| 3,998,222 A | 12/1976 | Shihata | |
| 4,076,023 A | 2/1978 | Martinez | |
| 4,133,312 A | 1/1979 | Burd | |
| 4,184,489 A | 1/1980 | Burd | |
| 4,214,586 A | 7/1980 | Mericle | |
| 4,318,401 A | 3/1982 | Zimmerman | |
| 4,366,819 A | 1/1983 | Kaster | |
| 4,427,219 A | 1/1984 | Madej | |
| 4,441,215 A | 4/1984 | Kaster | |
| 4,447,237 A | 5/1984 | Frisch et al. | |
| 4,496,349 A | 1/1985 | Cosentino | |
| 4,496,350 A | 1/1985 | Cosentino | |
| 4,503,568 A | 3/1985 | Madras | |
| 4,550,447 A | 11/1985 | Seiler, Jr. | |
| 4,619,641 A | 10/1986 | Schanzer | |
| 4,655,771 A * | 4/1987 | Wallsten | A61F 2/01 623/1.22 |
| 4,723,948 A | 2/1988 | Clark et al. | |
| 4,734,094 A | 3/1988 | Jacob et al. | |
| 4,753,236 A | 6/1988 | Healy | |
| 4,771,777 A | 9/1988 | Horzewski et al. | |
| 4,772,268 A | 9/1988 | Bates | |
| 4,786,345 A | 11/1988 | Wood | |
| 4,790,826 A | 12/1988 | Elftman | |
| 4,822,341 A | 4/1989 | Colone | |
| 4,848,343 A | 7/1989 | Wallsten et al. | |
| 4,850,999 A | 7/1989 | Planck | |
| 4,856,938 A | 8/1989 | Kuehn | |
| 4,877,661 A | 10/1989 | House et al. | |
| 4,898,591 A * | 2/1990 | Jang | A61L 29/049 604/264 |
| 4,898,669 A | 2/1990 | Tesio | |
| 4,917,067 A | 4/1990 | Yoshida | |
| 4,917,087 A | 4/1990 | Walsh et al. | |
| 4,919,127 A | 4/1990 | Pell | |
| 4,929,236 A | 5/1990 | Sampson | |
| 4,955,899 A | 9/1990 | Della Corna et al. | |
| 5,026,513 A | 6/1991 | House et al. | |
| 5,041,098 A | 8/1991 | Loiterman et al. | |
| 5,042,161 A | 8/1991 | Hodge | |
| 5,053,023 A | 10/1991 | Martin | |
| 5,061,275 A | 10/1991 | Wallsten et al. | |
| 5,061,276 A | 10/1991 | Tu et al. | |
| 5,064,435 A | 11/1991 | Porter | |
| 5,084,065 A | 1/1992 | Weldon et al. | |
| 5,104,402 A | 4/1992 | Melbin | |
| 5,171,227 A | 12/1992 | Twardowski et al. | |
| 5,171,305 A | 12/1992 | Schickling et al. | |
| 5,192,289 A | 3/1993 | Jessen | |
| 5,192,310 A | 3/1993 | Herweck et al. | |
| 5,197,976 A | 3/1993 | Herweck et al. | |
| 5,282,860 A | 2/1994 | Matsuno et al. | |
| 5,330,500 A | 7/1994 | Song | |
| 5,336,616 A * | 8/1994 | Livesey | A01N 1/00 435/1.3 |
| 5,399,168 A | 3/1995 | Wadsworth | |
| 5,404,320 A | 4/1995 | Twardowski et al. | |
| 5,405,320 A | 4/1995 | Twardowski et al. | |
| 5,405,339 A | 4/1995 | Kohnen et al. | |
| 5,454,790 A | 10/1995 | Dubrul | |
| 5,474,268 A | 12/1995 | Yu | |
| 5,474,563 A | 12/1995 | Myler et al. | |
| 5,476,451 A | 12/1995 | Ensminger et al. | |
| 5,496,294 A | 3/1996 | Hergenrother et al. | |
| 5,509,897 A | 4/1996 | Twardowski et al. | |
| 5,549,663 A * | 8/1996 | Cottone, Jr. | A61F 2/07 606/195 |
| 5,558,641 A | 9/1996 | Glantz et al. | |
| 5,562,617 A | 10/1996 | Finch, Jr. et al. | |
| 5,562,618 A | 10/1996 | Cai et al. | |
| 5,591,226 A | 1/1997 | Trerotola et al. | |
| 5,607,463 A | 3/1997 | Schwartz et al. | |
| 5,624,413 A | 4/1997 | Markel et al. | |
| 5,631,748 A | 5/1997 | Harrington | |
| 5,637,088 A | 6/1997 | Wenner et al. | |
| 5,637,102 A | 6/1997 | Tolkoff et al. | |
| 5,645,532 A | 7/1997 | Horgan | |
| 5,647,855 A | 7/1997 | Trooskin | |
| 5,669,637 A | 9/1997 | Chitty et al. | |
| 5,669,881 A | 9/1997 | Dunshee | |
| 5,674,272 A | 10/1997 | Bush et al. | |
| 5,676,346 A | 10/1997 | Leinsing | |
| 5,743,894 A | 4/1998 | Swisher | |
| 5,755,773 A | 5/1998 | Schuster | |
| 5,755,775 A | 5/1998 | Trerotola et al. | |
| 5,792,104 A | 8/1998 | Speckman et al. | |
| 5,797,879 A | 8/1998 | DeCampli | |
| 5,800,512 A | 9/1998 | Lentz et al. | |
| 5,800,514 A | 9/1998 | Nunez et al. | |
| 5,800,522 A | 9/1998 | Campbell et al. | |
| 5,810,870 A | 9/1998 | Myers et al. | |
| 5,829,487 A | 11/1998 | Thomas et al. | |
| 5,830,224 A | 11/1998 | Cohn et al. | |
| 5,840,240 A | 11/1998 | Stenoien et al. | |
| 5,866,217 A | 2/1999 | Stenoien et al. | |
| 5,904,967 A | 5/1999 | Ezaki et al. | |
| 5,931,829 A | 8/1999 | Burbank et al. | |
| 5,931,865 A | 8/1999 | Silverman et al. | |
| 5,957,974 A | 9/1999 | Thompson et al. | |
| 5,997,562 A | 12/1999 | Zadno-Azizi | |
| 6,001,125 A | 12/1999 | Golds et al. | |
| 6,019,788 A * | 2/2000 | Butters | A61B 17/064 604/8 |
| 6,036,724 A | 3/2000 | Lentz et al. | |
| 6,102,884 A | 8/2000 | Squitieri | |
| 6,156,016 A | 12/2000 | Maginot | |
| 6,167,765 B1 | 1/2001 | Weitzel | |
| 6,171,295 B1 | 1/2001 | Garabedian | |
| 6,231,085 B1 | 5/2001 | Olson | |
| 6,245,098 B1 | 6/2001 | Feeser | |
| 6,255,396 B1 | 7/2001 | Ding et al. | |
| 6,261,255 B1 | 7/2001 | Mullis et al. | |
| 6,261,257 B1 | 7/2001 | Uflacker et al. | |
| 6,280,466 B1 | 8/2001 | Kugler et al. | |
| 6,308,992 B1 | 10/2001 | Mitsui et al. | |
| 6,309,411 B1 | 10/2001 | Lashinski et al. | |
| 6,319,279 B1 | 11/2001 | Shannon et al. | |
| 6,338,724 B1 | 1/2002 | Dossa | |
| 6,398,764 B1 | 6/2002 | Finch, Jr. et al. | |
| 6,402,767 B1 | 6/2002 | Nash et al. | |
| 6,428,571 B1 | 8/2002 | Lentz et al. | |
| 6,436,132 B1 | 8/2002 | Patel et al. | |
| 6,582,409 B1 | 6/2003 | Squitieri | |
| 6,585,762 B1 | 7/2003 | Stanish | |
| 6,610,004 B2 | 8/2003 | Viole et al. | |
| 6,689,096 B1 | 2/2004 | Loubens et al. | |
| 6,689,157 B2 | 2/2004 | Madrid et al. | |
| 6,692,461 B2 | 2/2004 | Wantink | |
| 6,699,233 B2 | 3/2004 | Sianda et al. | |
| 6,702,748 B1 | 3/2004 | Nita et al. | |
| 6,702,781 B1 | 3/2004 | Reifart et al. | |

(56) References Cited

U.S. PATENT DOCUMENTS

| | | |
|---|---|---|
| 6,706,025 B2 | 3/2004 | Engelson et al. |
| 6,719,781 B1 | 4/2004 | Kim |
| 6,719,783 B2 | 4/2004 | Lentz et al. |
| 6,730,096 B2 | 5/2004 | Basta |
| 6,733,459 B1 | 5/2004 | Atsumi |
| 6,740,273 B2 | 5/2004 | Lee |
| 6,749,574 B2 | 6/2004 | O'Keefe |
| 6,752,826 B2 | 6/2004 | Holloway et al. |
| 6,758,836 B2 | 7/2004 | Zawacki |
| 6,858,019 B2 | 2/2005 | McGuckin |
| 6,926,724 B1 | 8/2005 | Chu |
| 6,926,735 B2 | 8/2005 | Henderson |
| 6,976,952 B1 | 12/2005 | Maini et al. |
| 6,981,987 B2 | 1/2006 | Huxel et al. |
| 7,011,645 B2 | 3/2006 | McGuckin, Jr. et al. |
| 7,025,741 B2 | 4/2006 | Cull |
| 7,044,937 B1 | 5/2006 | Kirwan et al. |
| 7,101,356 B2 | 9/2006 | Miller |
| 7,131,959 B2 | 11/2006 | Blatter |
| 7,211,074 B2 | 5/2007 | Sansoucy |
| 7,244,272 B2 | 5/2007 | White, II et al. |
| 7,244,271 B2 | 7/2007 | Lentz et al. |
| 7,252,649 B2 | 8/2007 | Sherry |
| 7,297,158 B2 | 11/2007 | Jensen |
| 7,351,257 B2 | 4/2008 | Kaldany |
| 7,399,296 B2 | 7/2008 | Poole et al. |
| 7,438,699 B2 | 10/2008 | Pecor et al. |
| 7,452,374 B2 | 11/2008 | Hain et al. |
| 7,507,229 B2 | 3/2009 | Hewitt et al. |
| 7,588,551 B2 | 9/2009 | Gertner |
| 7,708,722 B2 | 5/2010 | Glenn |
| 7,722,665 B2 | 5/2010 | Anwar et al. |
| RE41,448 E | 7/2010 | Squitieri |
| 7,762,977 B2 | 7/2010 | Porter et al. |
| 7,789,908 B2 | 9/2010 | Sowinski et al. |
| 7,828,833 B2 | 11/2010 | Haverkost et al. |
| 7,833,214 B2 | 11/2010 | Wilson et al. |
| 7,846,139 B2 | 12/2010 | Zinn et al. |
| 7,850,675 B2 | 12/2010 | Bell et al. |
| 7,850,705 B2 | 12/2010 | Bachinski et al. |
| 7,922,757 B2 | 4/2011 | McGuckin |
| 7,972,314 B2 | 7/2011 | Bizup et al. |
| 8,079,973 B2 | 12/2011 | Herrig et al. |
| 8,092,435 B2 | 1/2012 | Beling et al. |
| 8,313,524 B2 | 11/2012 | Edwin et al. |
| 8,388,634 B2 | 3/2013 | Rubenstein et al. |
| 8,512,312 B2 | 8/2013 | Sage |
| 8,551,139 B2 | 10/2013 | Surti et al. |
| 8,690,815 B2 | 4/2014 | Porter et al. |
| 8,951,355 B2 | 2/2015 | Boyle, Jr. et al. |
| 9,642,623 B2 | 5/2017 | Agarwal et al. |
| 9,731,113 B2 | 8/2017 | Grace et al. |
| 10,172,673 B2 | 1/2019 | Viswanathan et al. |
| 2001/0053930 A1 | 12/2001 | Kugler et al. |
| 2002/0049403 A1 | 4/2002 | Alanis |
| 2002/0055766 A1 | 5/2002 | Wallace et al. |
| 2002/0055771 A1 | 5/2002 | Sandock |
| 2002/0099432 A1 | 7/2002 | Yee |
| 2002/0151761 A1 | 10/2002 | Viole et al. |
| 2003/0100859 A1 | 5/2003 | Henderson et al. |
| 2003/0135258 A1 | 7/2003 | Andreas et al. |
| 2003/0135261 A1 | 7/2003 | Kugler et al. |
| 2003/0139806 A1 | 7/2003 | Haverkost et al. |
| 2003/0181969 A1 | 9/2003 | Kugler et al. |
| 2003/0212385 A1 | 11/2003 | Brenner et al. |
| 2003/0212431 A1 | 11/2003 | Brady et al. |
| 2004/0024442 A1 | 2/2004 | Sowinski et al. |
| 2004/0054405 A1 | 3/2004 | Thierry et al. |
| 2004/0069103 A1 | 4/2004 | Matteucci |
| 2004/0073282 A1 | 4/2004 | Stanish |
| 2004/0078071 A1 | 4/2004 | Escamilla et al. |
| 2004/0099395 A1 | 5/2004 | Wang et al. |
| 2004/0147866 A1 | 7/2004 | Blatter et al. |
| 2004/0193242 A1 | 9/2004 | Lentz et al. |
| 2004/0215058 A1 | 10/2004 | Zirps et al. |
| 2004/0215337 A1 | 10/2004 | Hain et al. |
| 2004/0236412 A1* | 11/2004 | Brar .............. A61B 17/12045 623/1.31 |
| 2005/0004553 A1* | 1/2005 | Douk .............. A61B 17/12022 604/523 |
| 2005/0137614 A1 | 6/2005 | Porter et al. |
| 2005/0192559 A1 | 9/2005 | Michels et al. |
| 2005/0203457 A1 | 9/2005 | Smego |
| 2005/0209581 A1 | 9/2005 | Butts et al. |
| 2005/0215938 A1 | 9/2005 | Khan et al. |
| 2006/0004392 A1 | 1/2006 | Amarant |
| 2006/0029465 A1 | 2/2006 | Auer |
| 2006/0058867 A1 | 3/2006 | Thistle et al. |
| 2006/0064159 A1 | 3/2006 | Porter et al. |
| 2006/0081260 A1 | 4/2006 | Eells et al. |
| 2006/0118236 A1 | 6/2006 | House et al. |
| 2007/0038288 A1* | 2/2007 | Lye .............. A61F 2/07 623/1.16 |
| 2007/0078412 A1 | 4/2007 | McGuckin, Jr. et al. |
| 2007/0078416 A1 | 4/2007 | Eliasen |
| 2007/0078438 A1 | 4/2007 | Okada |
| 2007/0088336 A1 | 4/2007 | Dalton |
| 2007/0123811 A1 | 5/2007 | Squitieri |
| 2007/0135775 A1 | 6/2007 | Edoga et al. |
| 2007/0142850 A1 | 6/2007 | Fowler |
| 2007/0161958 A1 | 7/2007 | Glenn |
| 2007/0167901 A1 | 7/2007 | Herrig et al. |
| 2007/0168019 A1 | 7/2007 | Amplatz et al. |
| 2007/0173868 A1 | 7/2007 | Bachinski et al. |
| 2007/0191779 A1 | 8/2007 | Shubayev et al. |
| 2007/0197856 A1 | 8/2007 | Gellman et al. |
| 2007/0213838 A1 | 9/2007 | Hengelmolen |
| 2007/0219510 A1 | 9/2007 | Zinn et al. |
| 2007/0233018 A1 | 10/2007 | Bizup et al. |
| 2007/0244539 A1 | 10/2007 | Lentz et al. |
| 2007/0249986 A1 | 10/2007 | Smego |
| 2007/0249987 A1 | 10/2007 | Gertner |
| 2007/0265584 A1 | 11/2007 | Hickman et al. |
| 2007/0293823 A1 | 12/2007 | Sherry |
| 2007/0293829 A1 | 12/2007 | Conlon et al. |
| 2008/0009781 A1 | 1/2008 | Anwar et al. |
| 2008/0027534 A1 | 1/2008 | Edwin et al. |
| 2008/0132924 A1 | 6/2008 | McGuckin |
| 2008/0167595 A1 | 7/2008 | Porter et al. |
| 2008/0221469 A1 | 9/2008 | Shevchuk |
| 2008/0306580 A1 | 12/2008 | Jenson et al. |
| 2009/0076587 A1 | 3/2009 | Cully et al. |
| 2009/0137944 A1 | 5/2009 | Haarala et al. |
| 2009/0179422 A1 | 7/2009 | Werth |
| 2009/0227932 A1* | 9/2009 | Herrig .............. A61M 1/3653 604/6.16 |
| 2009/0234267 A1 | 9/2009 | Ross |
| 2009/0318895 A1 | 12/2009 | Lachner |
| 2010/0154800 A1 | 6/2010 | Chang et al. |
| 2010/0160718 A1 | 6/2010 | Villafana et al. |
| 2010/0160847 A1 | 6/2010 | Braido et al. |
| 2010/0161040 A1 | 6/2010 | Braido et al. |
| 2010/0198079 A1 | 8/2010 | Ross |
| 2010/0268188 A1 | 10/2010 | Hanson |
| 2010/0268196 A1 | 10/2010 | Hastings et al. |
| 2010/0292774 A1* | 11/2010 | Shalev .............. A61F 2/07 623/1.13 |
| 2011/0015723 A1 | 1/2011 | Batiste et al. |
| 2011/0054312 A1 | 3/2011 | Bell et al. |
| 2011/0060264 A1 | 3/2011 | Porter et al. |
| 2011/0112482 A1 | 5/2011 | Redd |
| 2011/0208218 A1 | 8/2011 | Ball |
| 2011/0257609 A1 | 10/2011 | Bizup et al. |
| 2011/0264080 A1 | 10/2011 | Lim et al. |
| 2011/0295181 A1 | 12/2011 | Dann et al. |
| 2012/0059305 A1 | 3/2012 | Akingba |
| 2012/0065652 A1 | 3/2012 | Cully et al. |
| 2012/0078202 A1 | 3/2012 | Beling et al. |
| 2013/0060268 A1 | 3/2013 | Herrig |
| 2013/0338559 A1 | 12/2013 | Franano et al. |
| 2014/0018721 A1 | 1/2014 | Gage et al. |
| 2014/0094841 A1 | 4/2014 | Sutton et al. |
| 2014/0155908 A1 | 6/2014 | Rosenbluth et al. |
| 2014/0276215 A1 | 9/2014 | Nelson |

(56) References Cited

U.S. PATENT DOCUMENTS

| | | | |
|---|---|---|---|
| 2014/0288638 | A1 | 9/2014 | Knight et al. |
| 2014/0371779 | A1 | 12/2014 | Vale et al. |
| 2015/0051532 | A1 | 2/2015 | Tomko et al. |
| 2015/0082604 | A1 | 3/2015 | Cully et al. |
| 2015/0094744 | A1 | 4/2015 | Aghayev et al. |
| 2015/0150640 | A1 | 6/2015 | Boyle et al. |
| 2015/0257775 | A1 | 9/2015 | Gilvarry et al. |
| 2016/0066954 | A1 | 3/2016 | Miller et al. |
| 2016/0129177 | A1 | 5/2016 | Herrig |
| 2016/0136398 | A1 | 6/2016 | Heilman et al. |
| 2016/0279317 | A1 | 9/2016 | Gale et al. |
| 2017/0020556 | A1 | 1/2017 | Sutton et al. |
| 2019/0015627 | A1 | 1/2019 | Hall et al. |
| 2019/0022368 | A1 | 1/2019 | Hall et al. |
| 2019/0126017 | A1 | 5/2019 | Hall et al. |

FOREIGN PATENT DOCUMENTS

| | | |
|---|---|---|
| DE | 102008055587 | 8/2009 |
| EP | 0540834 | 5/1993 |
| EP | 1797831 | 6/2007 |
| JP | 57-14358 | 1/1982 |
| JP | 58-168333 | 11/1983 |
| JP | 62-112567 | 5/1987 |
| JP | 04-507050 | 12/1992 |
| JP | 05-212107 | 8/1993 |
| JP | 05-264468 | 12/1993 |
| JP | 06-105798 | 4/1994 |
| JP | 09-84871 | 3/1997 |
| JP | 09-264468 | 7/1997 |
| JP | 2003-501223 | 1/2003 |
| JP | 3995057 | 10/2007 |
| JP | 2008511414 | 4/2008 |
| KR | 101026933 | 4/2011 |
| KR | 20110036848 | 4/2011 |
| WO | WO 84/03036 | 8/1984 |
| WO | 199008509 | 8/1990 |
| WO | WO 95/19200 | 7/1995 |
| WO | WO 96/24399 | 8/1996 |
| WO | WO1998034676 | 8/1998 |
| WO | 2000027299 | 5/2000 |
| WO | WO 00/76577 | 12/2000 |
| WO | 200105447 | 1/2001 |
| WO | WO 01/05463 | 1/2001 |
| WO | WO2001028456 | 4/2001 |
| WO | 2004032991 | 4/2004 |
| WO | WO 04/112880 | 12/2004 |
| WO | WO2006026687 | 9/2006 |
| WO | 2009059371 | 5/2009 |
| WO | 2010059102 | 5/2010 |
| WO | 2011060386 | 5/2011 |
| WO | 2011153302 | 12/2011 |
| WO | 2015100251 | 7/2015 |

OTHER PUBLICATIONS

Co-Pending U.S. Appl. No. 12/688,716, filed Jan. 15, 2010 and its prosecution history.
European Search Report dated Dec. 3, 2013.
A.S. Coulson, M.D., Ph.D., Judy Quarnstrom, I.V.N., J. Moshimia, M.D., "A Combination of the Elephant Trunk Anastomosis Technique and Vascular Clips for Dialysis Grafts," Surgical Rounds, Nov. 1999, pp. 596 to 608.
L.C. Koo Seen Lin et al., "Contemporary Vascular Access Surgery for Chronic Haemodialysis," 1996 The Royal College of Surgeons of Edinburgh, J.R. Coll. Surg. Edinb., 41, June, 164-169.
Seshadri Raju, M.D., PTFE Grafts for Hemodialysis Access, "Techiques for Insertion and Management of Complications," Ann. Surg. vol. 206, No. 5, Nov. 1987, pp. 666-673.
Anatole Besarab et al., "Measuring the Adequacy of Hemodialysis Access," Current Opinion in Nephrology and Hypertension 1996, 5:527-531, Rapid Science Publishers ISSN 1062-4821.
Melhem J.A. Sharafuddin, MD et al., Dialysis Access Intervention, "Percutaneous Ballon-assisted Aspiration Thrombectomy of Clotted Hemodialysis Access Grafts," Journal of Vascular and Interventional Radiology, vol. 7, No. 2, Mar.-Apr. 1996, pp. 177-183.
David A. Kumpe et al. "Angioplasty/Thrombolytic Treatment of Failing and Failed Hemodialysis Access Sites: Comparison with Surgical Treatment," Progress in Cardiovascular Diseases, vol. XXXIV, No. 4 Jan./Feb. 1992: pp. 263-278.
Robert Y. Kanterman, MD et al., Intervention Radiology, "Dialysis Access Grafts: Anatomic Location of Venous Stenosis and results of Angioplasty," Radiology Apr. 1995, vol. 195, No. 1, 195: 135-139.
International Search Report and Written Opinion for PCT Application No. PCT/US2009/035923 dated Jun. 3, 2009 in 11 pages.
Alan S. Coulson, M.D., Jagjit Singh, M.D., Joseph C. Moya, "Modification of Venous End of Dialysis Grafts: An Attempt to Reduce Neointimal Hyperplasia," Dialysis & Transplantation, vol. 29, No. 1, Jan. 2000, pp. 10 to 18.
Davis, D. Peterson et al., "Subclavian venous stenosis: A complication of subclavian dialysis," The Journal of American Medical Association, vol. 252, No. 24, pp. 3404-3406, Dec. 28, 1984.
RE 41448 and its entire prosecution history. Jul. 20, 2012. Squitieri.
2006-0064159 and its prosecution history.
2007-0123811 and its prosecution history.
2005-0137614 and its prosecution history.
2007-0167901 and its prosecution history.
2008-0167595 and its prosecution history.
Besarab, et al.,Measuring the Adequacy of Hemodialysis Access, Current Opinion in Nephrology and Hypertension, Rapid Science Publishers ISSN ,1996 ,1062-4821.
European Search Report dated Jun. 8, 2005 for EP05006233.0.
European Search Report dated Dec. 3, 2013 for EP05793066.1.
International Preliminary Report dated Mar. 12, 2014 for PCT/US2012/053967.
International Search Report and Written Opinion dated Jan. 18, 2019 for PCT/US2018/041821.
International Search Report and Written Opinion dated Jan. 28, 2015 for PCT/US2014/049547.
International Search Report and Written Opinion dated Mar. 15, 2013 for PCT/US2012/053967.
International Search Report and Written Opinion dated Mar. 16, 2015 for PCT/US2014/046630.
International Search Report and Written Opinion dated Apr. 4, 2019 for PCT/US2018/058179.
International Search Report and Written Opinion dated May 2, 2018 for PCT/US2018/013326.
International Search Report and Written Opinion dated May 3, 2013 for PCT/US2012/053967.
International Search Report and Written Opinion dated May 6, 1998 for PCT/US1998/001939.
International Search Report and Written Opinion dated Jun. 15, 2018 for PCT/US2018/020614.
International Search Report and Written Opinion dated Jun. 20, 2007 for PCT/US2006/044564.
International Search Report and Written Opinion dated Jul. 17, 2018 for PCT/US2018/023956.
International Search Report and Written Opinion dated Oct. 30, 2018 for PCT/US2018/042900.
International Search Report and Written Opinion dated Jun. 22, 2018 for PCT/US2018/014371.
Notice of Allowance dated Mar. 15, 2010 for U.S. Appl. No. 11/216,536.
Notice of Allowance dated Oct. 4, 2013 for U.S. Appl. No. 12/831,092.
Notice of Allowance dated Oct. 5, 2018 for U.S. Appl. No. 15/093,622.
Notice of Allowance dated Nov. 6, 2018 for U.S. Appl. No. 14/995,270.
Office Action dated Jan. 8, 2019 for U.S. Appl. No. 15/035,626.
Office Action dated Jan. 9, 2018 for U.S. Appl. No. 14/450,468.
Office Action dated Feb. 6, 2013 for U.S. Appl. No. 12/831,092.
Office Action dated Mar. 15, 2018 for U.S. Appl. No. 14/332,091.
Office Action dated May 5, 2010 for U.S. Appl. No. 10/962,200.
Office Action dated May 24, 2018 for U.S. Appl. No. 14/995,270.
Office Action dated Jul. 11, 2018 for U.S. Appl. No. 14/450,468.
Office Action dated Jul. 19, 2018 for U.S. Appl. No. 15/035,626.

(56) References Cited

OTHER PUBLICATIONS

Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Sep. 20, 2012 for U.S. Appl. No. 12/831,092.
Office Action dated Oct. 1, 2018 for U.S. Appl. No. 14/332,091.
Office Action dated Nov. 26, 2007 for U.S. Appl. No. 10/962,200.
Office Action dated Dec. 5, 2017 for U.S. Appl. No. 14/995,270.
Office Action dated Dec. 5, 2018 for U.S. Appl. No. 14/450,468.
Office Action dated Dec. 30, 2016 for U.S. Appl. No. 14/450,468.
Clinical Reveiw of MTI, Onxy Liquid Embolization System, available at http://www.fda.gov/ohrms/dockets/ac/03/briefing/3975b1-02-clinical-review.pdf. accessed Aug. 29, 2005.
Kanterman, et al.,Dialysis Access Grafts: Anatomic Location of Venous Stenosis and Results of Angioplasty, Interventional Radiology, vol. 195 No. 1, 195 ,Apr. 1995 ,135-139.
Sharafuddin, et al.,Percutaneous Balloon-Assisted Aspiration Thrombectomy of clotted ahemodialysis Access Grafts, Journal of Vascular and Interventional Radiology, vol. 7 No. 2 ,Mar.-Apr. 1996,177-183.
Office Action dated Sep. 26, 2019 for U.S. Appl. No. 15/693,010.
Office Action dated Apr. 16, 2020 for U.S. Appl. No. 15/868,313.
Office Action dated May 1, 2020 for U.S. Appl. No. 15/693,010.
Office Action dated May 5, 2020 for U.S. Appl. No. 15/910,273.

\* cited by examiner

IMPLANTABLE AND REMOVABLE CUSTOMIZABLE BODY CONDUIT

CROSS-REFERENCE TO RELATED APPLICATIONS

This application is a divisional of U.S. application Ser. No. 13/151,157, filed Jun. 1, 2011, which is a continuation-in-part of U.S. application Ser. No. 12/397,275, filed Mar. 3, 2009, which claims priority to and the benefit of U.S. Provisional Application No. 61/034,125, filed Mar. 5, 2008, which are all hereby incorporated by reference herein in their entirety. Each of the following applications also is incorporated by reference herein in its entirety: U.S. application Ser. No. 11/600,589, filed Nov. 16, 2006; U.S. application Ser. No. 11/216,536 filed on Aug. 31, 2005; and U.S. application Ser. No. 10/962,200, filed on Oct. 8, 2004.

BACKGROUND OF THE INVENTIONS

Field of the Inventions

This application relates to systems and methods for treating or bypassing stenosis in a body conduit, and connecting multiple portions of fluid carrying conduits.

Description of the Related Art

In the United States, approximately 400,000 people have end-stage renal disease requiring chronic hemodialysis. Permanent vascular access sites for performing hemodialysis may be formed by creating an arteriovenous (AV) anastomosis whereby a vein is attached to an artery to form a high-flow shunt or fistula. A vein may be directly attached to an artery, but it may take 6 to 8 weeks before the venous section of the fistula has sufficiently matured to provide adequate blood flow for use with hemodialysis. Moreover, a direct anastomosis may not be feasible in all patients due to anatomical considerations. Other patients may require the use of artificial graft material to provide an access site between the arterial and venous vascular systems.

Although many materials that have been used to create prosthetic grafts for arterial replacement have also been tried for dialysis access, expanded polytetrafluoroethylene (ePTFE) is the preferred material. The reasons for this include its ease of needle puncture and particularly low complication rates (pseudo-aneurysm, infection, and thrombosis). However, AV grafts still require time for the graft material to mature prior to use, so that a temporary access device, such as a Quinton catheter, must be inserted into a patient for hemodialysis access until the AV graft has matured. The use of temporary catheter access exposes the patient to additional risk of bleeding and infection, as well as discomfort. Also, patency rates of ePTFE access grafts are still not satisfactory, as the overall graft failure rate remains high. Sixty percent of these grafts fail yearly, usually due to stenosis at the venous end. (See Besarab, A & Samararpungavan D., "Measuring the Adequacy of Hemodialysis Access". *Curr Opin Nephrol Hypertens* 5(6) 527-531, 1996, Raju, S. "PTFE Grafts for Hemodialysis Access". *Ann Surg* 206(5), 666-673, November 1987, Koo Seen Lin, LC & Burnapp, L. "Contemporary Vascular Access Surgery for Chronic Hemodialysis". *J R Coll Surg* 41, 164-169, 1996, and Kumpe, D A & Cohen, M A H "Angioplasty/Thrombolytic Treatment of Failing and Failed Hemodialysis Access Sites: Comparison with Surgical Treatment". *Prog Cardiovasc Dis* 34(4), 263-278, 1992, all herein incorporated by reference in their entirety). These failure rates are further increased in higher-risk patients, such as diabetics. These access failures result in disruption in the routine dialysis schedule and create hospital costs of over $2 billion per year. See Sharafuddin, M J A, Kadir, S., et al. "Percutaneous Balloon-assisted aspiration thrombectomy of clotted Hemodialysis access Grafts". *J Vasc Intery Radiol* 7(2) 177-183, 1996, herein incorporated by reference in its entirety.

Many individuals have vascular segments that are stenosed, narrowed, occluded, or otherwise compromised to inhibit flow. This is frequently a problem in dialysis patients due to placement of previous catheters for dialysis access, as described by Davis, D, Petersen, J, Feldman, R, et al. *Subclavian venous stenosis. A complication of subclavian dialysis*. JAMA 1984; 252:3404. The stenosis is commonly caused by dialysis catheters presence in the subclavian vein. Edema, pain and discomfort in the arm are frequently reported in these individuals. These side effects are often accelerated during dialysis sessions.

SUMMARY OF THE INVENTIONS

In one method, a stenosis is treated to improve the patency of a vascular segment. In the method, a delivery device is provided that has an elongate tubular member coupled therewith. The elongate tubular member has an outside surface that is configured to prevent adherence of in vivo matter. For example, a very smooth and impermeable surface can be provided. As discussed below, silicone is a material that can have such properties. The tissue and vasculature response is minimal due to the biocompatibility, surface finish, lack of porosity and possibly compliance and/or surface energy of silicone. Other materials providing comparable properties in one or more of these areas may be suitable substitutes, as elaborated below. The tubular member has a proximal end and a distal end and is reinforced along its length to maintain open lumen under a transverse load. The delivery device and the tubular member are advanced into the vasculature such that the distal end of the elongate tubular member is disposed distal of a stenosis. The proximal end of the elongate tubular member is disposed inside the vessel, preferably at a location proximal of the stenosis. Thereafter, the elongate tubular member is separated from the delivery device to deploy the elongate tubular member. The deployed elongate tubular member remains in the body as the delivery device is removed. The deployed elongate tubular member provides a stenting or dilating effect and thereby displaces the stenosis radially outward and expands the vessel lumen. Thereafter, after a therapeutic period, the elongate tubular member is removed intact. The therapeutic period can be defined as one in which remodeling of the vessel occurs.

As used herein "remodeling" is a broad term and includes the durable widening of a previously narrowed body vessel to a larger size, permitting a greater degree of flow, less flow resistance, less back pressure, and/or other flow benefits. The embodiments described herein can find application in any body conduit, such as any blood vessel. Arterial and venous vessels can be treated with these apparatuses and methods. Also, a variety of such vessels of different size and body regions can be treated. This method can be applied anywhere in the vasculature, but is has been tested with great success in the venous vasculature. Other body lumens outside the vascular system can be treated as well, including the esophagus, respiratory and nasal passages, lumens of the gastro-intestinal track, urinary tract, biliary duct.

A delivery device can be provided that is configured to couple with the elongate tubular member to apply an axial force, e.g., an tensile axial force, to actuate the elongate tubular member from an expanded configuration capable of providing the open lumen, as discussed above, to a low crossing profile configuration. The delivery device can be advanced with the tubular member disposed thereon or therein in the low crossing profile configuration. The delivery device can be configured to release the tensile axial force to permit the tubular member to move from the low crossing profile configuration to the expanded configuration.

In various applications, the treatment envisions removing the tubular member after a therapeutic period. In other words, the tubular member is intended to be a temporary implanted structure. The therapeutic period can be as few as 1 day. In some cases, the therapeutic period can be up to 12 months. Significant permanent benefit may take approximately 2 months.

In another aspect, a method of bypassing a stenosis in the vasculature is provided. In this method, a first graft member is coupled with a first vessel segment upstream of the stenosis and a second graft member is coupled with a second vessel segment downstream of the stenosis. A first end of the blood flow conduit is coupled with the first graft member and a second end of the blood flow conduit with the second graft member by applying a connection force, e.g., providing relative motion between an end of the blood flow conduit and a connector disposed on an end of one of the graft members. Both the first and second ends of the blood flow conduit are disposed outside the vasculature. When the first and second grafts are connected to the blood flow conduit, a force required to disconnect the blood flow conduit from the first or second graft is significantly higher than the connection force. In some variations of this method, one or both of the first and at least a portion of the blood flow conduit are disposed beneath the skin of the patient.

In another aspect, a method bypasses a stenosis and provides vascular access for a periodic therapeutic procedure, such as hemodialysis. A distal blood conduit and a proximal blood conduit comprising a graft and a connector are provided. The connector has a retention feature located thereon. The distal blood conduit includes a catheter comprising a braided structure embedded therein. A distal zone of the distal blood conduit is inserted into the vasculature and through a stenosis in the vasculature. In some embodiments, the distal end includes an outlet and the outlet is positioned anywhere beyond the stenosis but still within the vasculature. Downstream of the distal end, the blood exits the blood conduit and rejoins flow in the cardiovascular system.

Though not required in all methods of bypassing a stenosis and providing vascular access, the catheter can be cut through the braided structure to size the catheter in-situ. The catheter is advanced over a distal segment of the connector until at least a portion of the braided structure is positioned proximal of the retention feature. Also, although this method has been discussed herein in the context of a multi-component blood conduit, for bypassing a stenosis and providing vascular access, not all embodiments need be multi-component.

Furthermore, in certain variations of this method of bypassing a stenosis and providing vascular access, it is desired to also provide a treatment in which the stenosis is remodeled. A variety of techniques for configuring a conduit to provide for remodeling are discussed herein and can be used to provide remodeling in conjunction with bypassing a stenosis and providing vascular access.

In another aspect, a system for bypassing a stenosis is provided. The system includes a catheter, a first connector, and a second connector. The catheter has a proximal portion, a distal portion, and an elongate body extending between the proximal and distal portions. The elongate body defined an inner wall having an inner perimeter defining a blood flow lumen. The catheter has a braided structure embedded in the elongate body and disposed about the lumen. The first connector is for fluidly coupling a first vascular graft with the proximal portion of the catheter. The first connector comprises a connector body and an engagement feature. The connector body has an outer surface defining a first outer perimeter and an inner surface defining a lumen. The engagement feature is disposed on the outer surface of the connector body adjacent a distal end thereof. The engagement feature defines a second outer perimeter greater than the first outer perimeter. The second connector is configured to securely engage a second vascular graft with the distal portion of the catheter. The proximal portion of the catheter has a first configuration in the free state and a second configuration when in axial compression. In the first configuration, the inner perimeter is less than the first outer perimeter. In the second configuration, the braided structure expands to permit the inner perimeter of the catheter body to expand such that the proximal end portion of the catheter can be advanced over the engagement feature of the connector body.

BRIEF DESCRIPTION OF THE DRAWINGS

The structure and method of using the invention will be better understood with the following detailed description of embodiments of the invention, along with the accompanying illustrations, in which.

DETAILED DESCRIPTION OF THE PREFERRED EMBODIMENT

Figure 1:
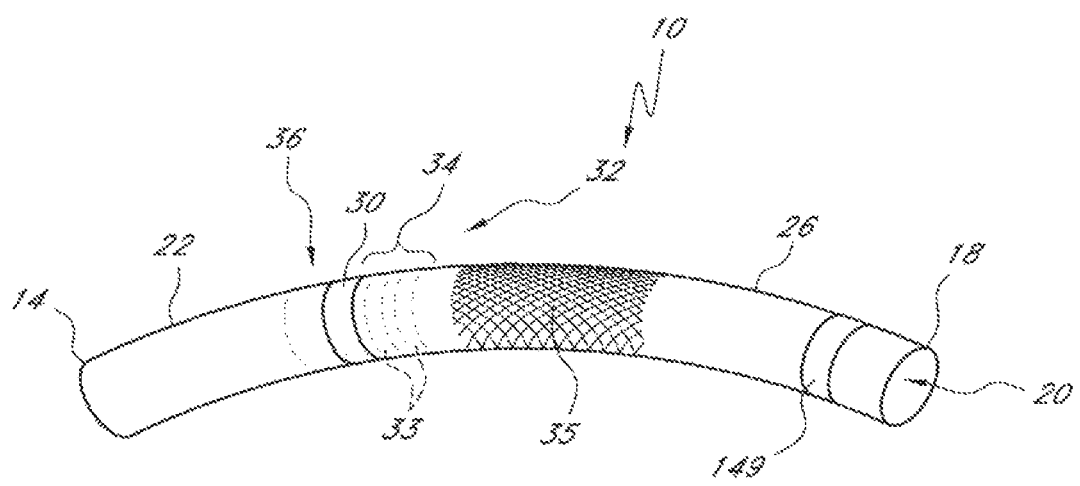
FIG. 1 is a perspective view of a vascular access system having a proximal end adapted to couple with a first vascular segment and a distal end adapted for insertion into a second vascular segment.

This application relates to new vascular access systems, new connector systems, and new fluid-carrying conduits. The fluid carrying conduits are arteriovenous (AV) shunts or catheters in various embodiments. Some of the embodiments described herein may be incorporated into a hemodialysis system. These embodiments also can be used to treat or bypass stenoses in the vasculature, as discussed below.

Hemodialysis treatments and vascular access devices therefore are discussed in greater detail in U.S. patent application Ser. No. 10/962,200 (US Publication No. 2005-0137614-A1), Ser. No. 11/216,536 (US Publication No. 2006-0064159 A1), and Ser. No. 11/600,589 (US Publication No. 2007-0167901 A1) and in U.S. Pat. Nos. 6,102,884 and 6,582,409. The embodiments described herein can be combined with the systems and methods of any of these applications and patents, all of which are hereby incorporated by reference in their entirety.

As will be understood in view of the description herein provided, the new connector systems and apparatuses can improve one or more areas of performance of vascular access systems. For example, the embodiments described herein improve in-situ connection of a catheter, or other blood-carrying conduit, configured for use as an outflow component, to another component or device of a vascular access system or to a plurality of other components of a bypass system.

In some embodiments, a reinforcement member can be incorporated into a blood conveying system (e.g., in a proximal portion of a catheter or other blood carrying conduit) to enhance the security of a connection between a catheter and another component of the system. In some cases, the reinforcement member also extends through a substantial portion of the length of a blood carrying conduit to improves kink and crush resistance of the fluid carrying conduit. The reinforcement can also provide enhanced hoop strength or outwardly directed hoop stress to displace tissue, e.g., subcutaneous tissue around blood vessels or stenotic matter creating blockages in vessels. These and other advantages of the new devices and methods described herein could be useful in a number of environments that employ a vascular access system, such as vascular access devices, ventricular assist devices, total artificial hearts, and various types of hemodialysis systems.

Environments in which these improvements could be used include short-term applications (e.g., several days to a week) and longer-term application. For example, the improvements described herein are useful in longer-term applications of 30 days or more. The improvements described herein are useful in longer-term applications of 90 days or more. In some cases, the improvements described herein are useful in long-term applications of 1 year or more. The embodiments described herein can be incorporated into short-term and into longer-term applications for dialysis. Discussed further below in connection with FIG. 9, certain apparatuses discussed herein could be used or modified by use as temporary stents to assist in remodeling the vasculature to improve patency during and after a therapeutic period.

As will be discussed below, a braided structure can be incorporated into a fluid-carrying conduit. In some embodiments, the braided structure can be embedded in an elongate body of the fluid-carrying conduit, providing a smooth relatively constant outer surface. The braided structure can improve the security or integrity of the connection between the blood-carrying conduit and other structures to which it is attached. In various embodiments, these innovations provide greater durability and manufacturability. In addition, the implantation process can be enhanced, such as by providing better connectability and, in some cases, a tactile confirmation of the security of a connection, as discussed below. In some cases, a visual confirmation of the security of a connection can be provided.

Figure 10:
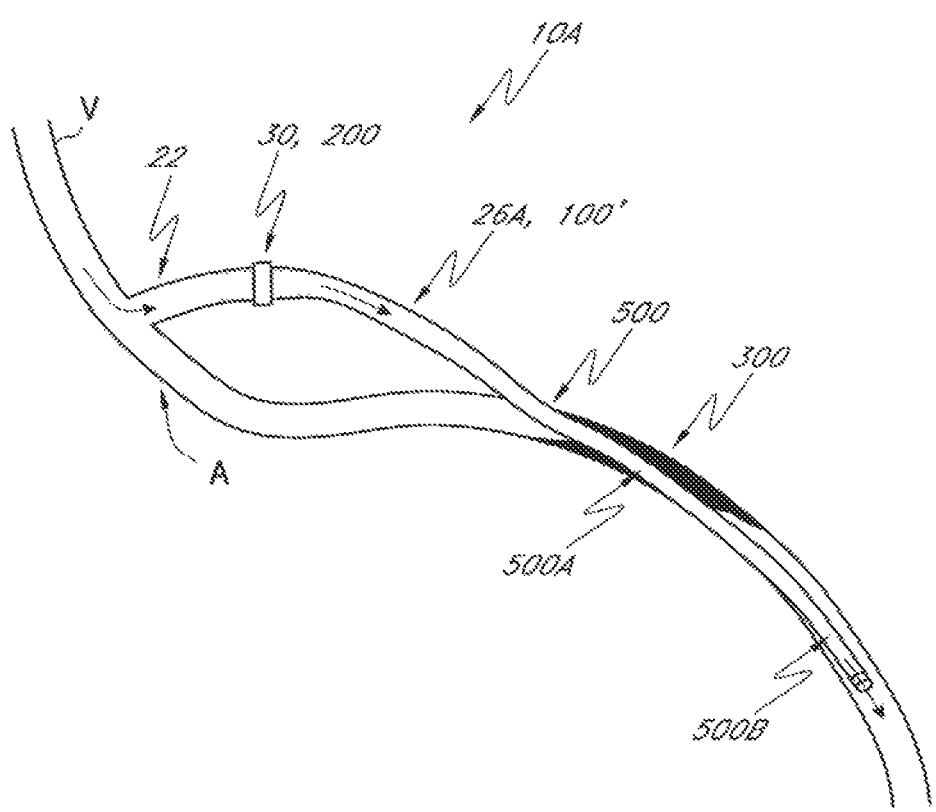
FIG. 10 illustrates a method of bypassing a stenosis.
Figure 11:
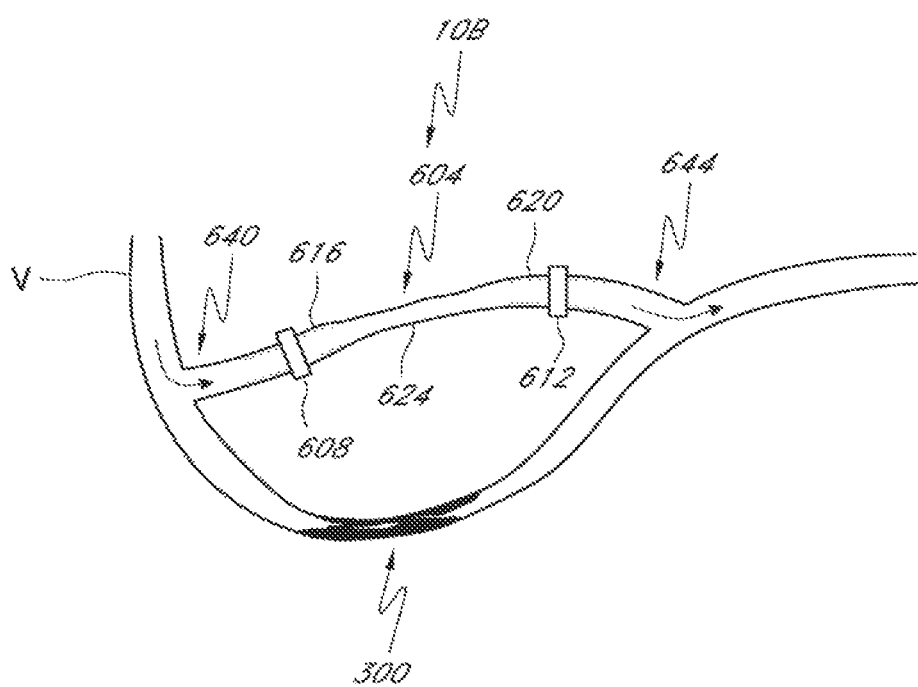
FIG. 11 illustrates a system for and method of bypassing a stenosis in the vasculature.

FIG. 1 depicts one embodiment of a vascular access system 10 that is configured to shunt blood from a first vascular segment to a second vascular segment. The vascular access system 10 can take any suitable form, but preferably the system is adapted to be implanted beneath the skin of the patient. In one embodiment, the vascular access system 10 is implanted primarily extravascularly, though a distal portion thereof may reside in or extend through a blood vessel. The vascular access system 10 can be partly or completely implanted. Various techniques for implanting are discussed below, including placement of at least a portion of the system 10 in a vascular segment. FIG. 10 illustrates methods of using a catheter system 10A similar to the access system FIG. 1 to provide improved blood flow through a stenotic region of a blood vessel. In this method, the system 10A can be used solely for improving patency through the stenosis or both for improved flow and access during a dialysis or other periodic therapeutic procedure. Also, a catheter system 10B similar to the vascular access system 10 can be implanted in a subcutaneous tunnel, as discussed further below. FIG. 11 illustrates catheter system 10B that is configured to provide bypass of a stenotic vascular segment where the system 10B is disposed in a subcutaneous tunnel. Additional details of processes for implantation are discussed in the patents and applications listed above, which are incorporated by reference herein.

With continued reference to FIG. 1, the vascular access system 10 has a proximal end 14 and a distal end 18 and a lumen 20 that extends between the proximal and distal ends 14, 18. The proximal end 14 can be adapted to couple with, e.g., attached to, a first vascular segment and the distal end 18 can be adapted to be coupled with, e.g., inserted into a second vascular segment. The lumen 20 preferably extends between the proximal and distal ends 14, 18 and provides a pathway for blood to flow between the first and second vascular segments. The lumen 20 also can be accessed from outside the patient to facilitate dialysis or other treatment. In some applications and embodiments, the lumen 20 provides blood flow from an upstream to a downstream location without any periodic access required or anticipated.

The first and second vascular segments are arterial or venous vascular segments in various techniques. For example, the proximal end 14 can be adapted to be coupled with a brachial artery or other artery that resides close to the skin. Any suitable coupling between the proximal end 14 and the first vascular segment can be used. In one embodiment the proximal end 14 can be attached by an end-to-side anastomosis to a brachial artery. The distal end 18 can be adapted to couple with or extend into a vein, e.g., in the central venous system, as discussed below and in the application incorporated by reference herein.

In one embodiment, the vascular access system 10 includes a plurality of components that can be assembled to form the lumen 20. In one embodiment, a first blood carrying conduit 22 extends from the proximal end 14 toward the distal end 18 and a second blood carrying conduit 26 extends from the distal 18 toward the proximal end 14.

In one embodiment a third blood carrying conduit 30 is positioned between the first and second blood carrying conduits 22, 26. As discussed below, the third blood carrying conduit 30 is adapted to connect the first and second blood carrying conduits 22, 26 together in various embodiments.

Where provided, the third blood carrying conduit 30 enables the first and second blood carrying conduits 22, 26 to have different characteristics that are well suited for the unique ways in which these conduits interact with the vasculature. For example, the first blood carrying conduit 22 can be specifically configured to be integrated into the vessel with which it is coupled, e.g., by anastomosis connection to an artery. Also, the second blood carrying conduit 26 can be specifically configured to interact with a vascular segment to minimize the likelihood of adverse side effects, e.g., by being flexible or otherwise formed to enable a distal portion of the conduit 26 to extend into the central venous system and interact in an atraumatic manner with vessel walls and other tissues in the vasculature or heart. Thus, this innovation pertains to the unique requirements of a device that perform both as a permanently implanted extravascular graft and as an intravascular catheter.

FIG. 11 illustrates embodiments in which one or more additional blood carrying conduits may be incorporated into a system 10B to provide a bypass system. As discussed above, this can enable end portions to couple with blood vessels and a central portion to have an enhanced patency configuration.

The vascular access system 10 and the bypass system 10B can be configured with one or more engagement mechanism 32 that enhances the security of a connection between two blood carrying conduits of the system. The engagement mechanism 32 can include multiple portions with at least one portion located on the second blood carrying conduit 26 and at least one portion is located on the third blood carrying conduit 30. In some embodiments, the engagement mechanism 32 is configured such that the connection formed thereby requires a greater force to disconnect than is required to connect the second and third blood carrying conduits 26, 30. This provides greater security of and confidence in the connection at the engagement mechanism 32.

In various embodiments, the engagement mechanism 32 includes an engagement feature 33 located on one of the second and third blood carrying conduits 26, 30 and an enlargeable portion 34 on the other of the second and third blood carrying conduits 26, 30. For example, as discussed in more detail below, the third blood carrying conduit 30 can include at least one barb and the second blood carrying conduit 26 can be formed to apply an inward and sometimes distally directed force on the barb to resist disconnection of the conduits. In one embodiment, a distal portion of the third blood carrying conduit 30 includes two barbs. In one embodiment, the second blood carrying conduit 26 includes a braided structure or other expandable reinforcement member 35 that generates a compressive force on the barb or barbs to enhance the security of the engagement mechanism 32. FIG. 1 only shows the braided structure partially for clarity. As discussed further below, the braided structure can extend to the proximal end 14 and toward the distal end 18. Various additional examples of features of engagement mechanisms are discussed below.

In some embodiments, the vascular access system 10 also includes an engagement mechanism 36 that facilitates coupling the first blood carrying conduit 22 with a distal portion of the lumen 20. As discussed further below, the engagement mechanism 36 can be incorporated into a proximal portion of a connector. In other embodiments, the first and third conduits 22, 30 can be unitary in construction such that the engagement mechanism 36 is not required.

The first blood carrying conduit 22 can take any suitable form for providing fluid communication between a patient's vascular system and the lumen 20. In one form the first blood carrying conduit 22 is a graft formed of a suitable material, e.g., ePTFE. In some applications, it is desirable to provide access to the lumen 20 very soon after implantation of the system 10. Various features for enabling access very soon after implantation, if not immediately thereafter, are discussed in the applications incorporated by reference herein above, including U.S. application Ser. No. 11/216,536 (US Publication No. 2006-0064159 A1) and Ser. No. 11/600,589 (US Publication No. 2007-0167901 A1). Other suitable biocompatible materials can be used and these will be apparent to one skilled in the art.

Although illustrated in an AV shunt context, the engagement mechanism is also relevant to other context. Accordingly, the first blood carrying conduit 22 could be a proximal portion of a connector, or a component of another system that conveys blood, e.g., in a ventricular assist device. Also, as discussed in connection with FIGS. 10-11, the engagement mechanism can be useful for systems and methods directed to bypassing a stenosis.

In one embodiment, the second blood carrying conduit 26 is configured as a catheter for returning blood to a patient's vasculature. In some embodiments, the conduit 26 is an outflow component of the system 10. The catheter preferably is adapted such that, in use, at least a distal end portion thereof can freely float within a vascular segment when the vascular access system 10 is applied to a patient. This feature reflects research that indicates that graft failures from localized stenosis at the venous end of AV grafts are primarily due to intimal hyperplasia, compliance mismatch between the graft and the native vein anastomosis, and turbulent flow at the anastomosis site. Kanterman R. Y. et al. "Dialysis access grafts: Anatomic location of venous stenosis and results of angioplasty." Radiology 195: 135-139, 1995. We hypothesize that these causes could be circumvented by eliminating the venous anastomosis and instead, using a fluid carrying conduit to discharge the blood directly into the venous system. We have developed vascular access system that eliminates the venous anastomosis in the AV shunt, using a catheter element at the venous end and a synthetic graft element anastomosed to the artery in the standard fashion. We believe that such system should eliminate or reduce venous hyperplasia, which is the largest reason for AV shunt failure.

Accordingly, at least a portion of the second blood carrying conduit 26 (e.g., a distal portion thereof) can be configured to freely float to provide atraumatic interaction with the blood vessel. Such a configuration also can minimize the likelihood of damage to the vessel in which the distal end portion resides by minimizing trauma to the vessel. This approach is also relevant to the bypass technique of FIG. 10, discussed below, where a first zone is configured to expand into engagement with and in fact remodel a stenosis while a second zone is configured to freely float to minimize adverse trauma at the second zone.

In some embodiments, the conduit 30 or portions thereof can be integrated into another component, e.g., into the first blood carrying conduit 22. Thus, the system 10 can be configured with less than three, e.g., only two, separate blood carrying conduits. Additionally, the primary function of the third blood carrying conduit 30 is to couple the first and second blood carrying conduits 22, 26 and thus the third blood carrying conduit need not be exposed to blood or form a part of the lumen 20 in all embodiments.

Figure 2:
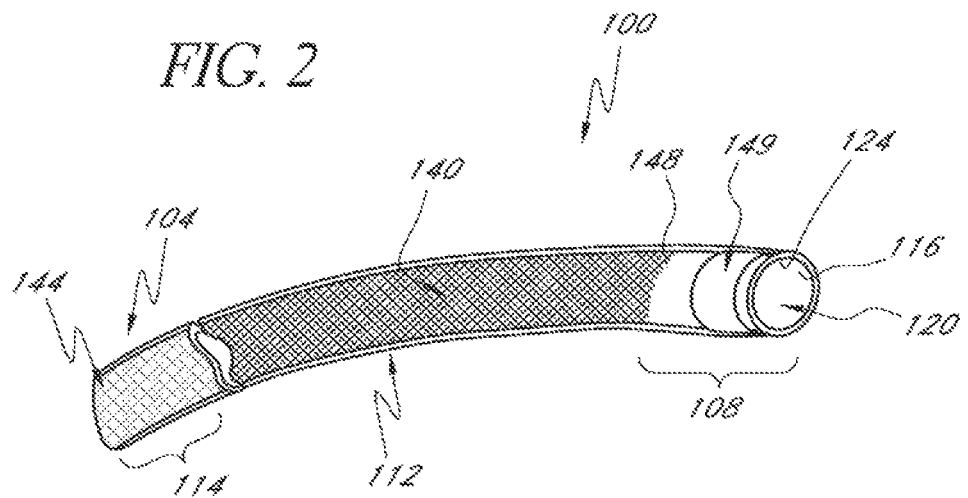
FIG. 2 is a perspective view of a catheter that has a distal portion adapted for positioning in a blood vessel and a proximal portion configured to provide an enhanced connection to another blood conduit.

FIG. 2 shows one embodiment of a catheter 100 that can be used in the vascular access system 10. As used herein "catheter" is a broad term that includes any blood carrying conduit that can be at least partially inserted into a blood vessel and advanced therein to a selected location, including into the atrium. The catheter 100 can take any suitable form, consistent with the below description. In some embodiments, the catheter is configured as an outflow component.

The catheter 100 has a proximal portion 104, a distal portion 108, and an elongate body 112 that extends therebetween. In some applications, the catheter 100 is configured such that the proximal portion 104 is connectable over a barb, as discussed below, to enhance securement of the catheter 100 to a connector, which can be incorporated into the conduit 30. The proximal portion 104 preferably also is trimmable such that the length of the catheter 100 can be determined in-situ. In one embodiment, the catheter 100 also has a sizing region 114 that facilitates customizing the size of the catheter 100 to the patient. In one embodiment, the sizing region 114 is located in the proximal portion 104 of the catheter 100. As will be discussed further below, the sizing region 114 can be trimmed or cut through to reduce the length of the catheter 100. Preferably the sizing region 114 is configured to be cut by hand using any standard cutting implement that would be present in the operating room, such as surgical scissors.

The elongate body 112 preferably defines an inner wall 116 that surrounds a blood flow lumen 120. The inner wall 116 has an inner perimeter 124 that in part defines the blood flow capacity of the catheter 100. In one embodiment, the blood flow lumen 120 is substantially cylindrical and the inner wall 116 and the inner perimeter 124 define are substantially circular in cross-section. In one embodiment, the blood flow lumen 120 has an inner diameter of about 5.0 mm. Lumens of other shapes can be used as well, as will be understood by one skilled in the art. Forming the lumen 120 to have a 5.0 mm diameter lumen provides a benefit of being able to handle sufficient blood flow for dialysis while permitting the outer size of the catheter 100 to be small enough to be insertable into the internal jugular vein in one technique. The outer size and inner perimeter 124 of the catheter 100 can be substantially constant through the length of the lumen 120 or can vary as will be understood by one skilled in the art.

Figure 9:
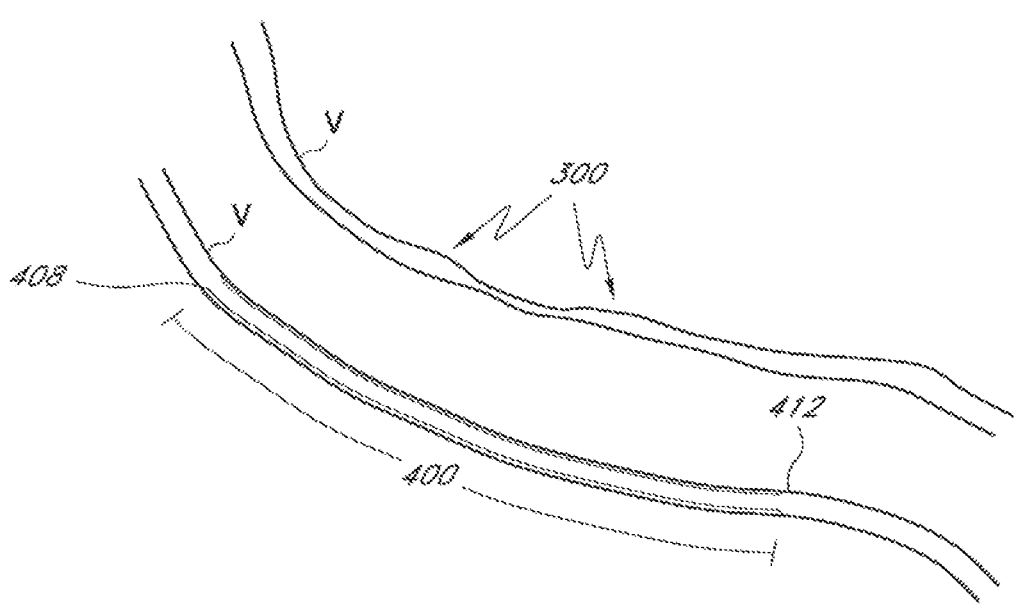
FIG. 9 illustrates schematically a method of treating a stenosis in a blood vessel using an elongate tubular member.

FIG. 9 below discusses using a stent 400 with a configuration that is similar to that of the catheter 100. Accordingly, the features of the catheter 100 are incorporated below in the discussion of the stent 400. The stent 400 may have an inner perimeter, e.g., diameter, of anywhere from 1.0-15 mm depending on the applications. A variety of embodiments for vascular therapies have an expanded size in the range of about 5.0 mm to about 14.0 mm. In some embodiments particularly suited for neurological therapies, the stent 400 can be configured to expand to an inner size of between about 2.0 mm and about 4.0 mm. In other embodiments particularly suited for therapies in carotid vessels, the stent 400 can be configured to expand to an inner size of between about 6.0 mm and about 10.0 mm.

The elongate body 112, particularly the inner wall 116 can be configured to provide adequate hemocompatibility such that blood flowing therethrough is not damaged or adversely affected thereby. The blood flow lumen 120 preferably is configured to convey blood in a substantially atraumatic manner between the portions 104, 108. In one embodiment the inner wall 116 is sufficiently smooth in surface finish to minimize turbulence at the wall. If the catheter 100 is integrated into the vascular access system 10 (e.g., as the second blood carrying conduit 26), the lumen 120 can form a portion of the lumen 20. Other portions of the lumen 20 can be defined in one or both of the first and third blood carrying conduits 22, 30.

The catheter 100 preferably is configured such that in use the distal portion 108 can freely float within a vascular segment. As discussed elsewhere herein, the system 10 can be applied such that the distal portion 108 is positioned in, extends within, or is inserted through a blood vessel, e.g., in the central venous system. Accordingly, the distal portion 108 preferably is configured to have a smaller outer size than the vessel in which it resides. This enables blood to pass around the distal end portion 108. For example, the distal portion 108 can reside in the central venous system in such a manner that blood flows between an outer surface of the distal portion 108 and an inner surface of the blood vessel. In one embodiment, the distal portion 108 of the catheter 100 has an outer perimeter that is substantially circular with an outer diameter of about 6.1 mm. In comparison, the typical vessel through which the distal portion 108 can be inserted is about 8-20 mm. In some patients, a portion of the central venous system, e.g., the internal jugular vein, can be stenosed, reducing its size significantly. In some cases, the internal jugular vein has a lumen that is as small as 0 to 1 mm in width. These patients may benefit form a method and a device capable of enlarging the lumen in the internal jugular vein or other vessel of the central venous system, as discussed below. Although larger catheters can be used for some patients and for some other applications, 6.1 mm is a size that is particularly well suited for insertion into an internal jugular vein of an adult human patient. Smaller catheters can be used for certain techniques, e.g., for more peripheral applications.

FIG. 10 illustrates a bypass application, in which a zone of a catheter 100' between the distal portion and the proximal portion thereof is large enough to engage a stenotic lesion, e.g., having an outside diameter that is larger than non-stenotic vessel bore by a percentage appropriate to compensate for vessel recoil upon withdrawal. For example, recoil observed during angioplasty of veins and arteries with interventional techniques is typically 20-30%. The venous system is more elastic and therefore may be on the upper end of this range. It is anticipated that the invention will take up to or less than this amount due to the longer treatment period (stent implant vs. balloon intervention). Therefore, in various embodiments, the outer perimeter (e.g., diameter) is about 20-30% larger than the non-stenotic vessel bore to produce the therapeutic effect. In some treatments, e.g., with longer therapeutic period, the outer perimeter (e.g., diameter) is larger than the non-stenotic vessel bore by up to about 20% to produce the therapeutic effect. One embodiment provides for sizing the stenosis engagement zone at about 20% of the non-stenotic vessel bore where the therapeutic period is at least about 2 months to produce the therapeutic effect.

The dimensions of the system 10 and the components described herein that can be used in the system 10 are not limiting. Rather the dimensions provide examples of specific embodiments. For other applications, other dimensions may be appropriate. For example, the outer diameter of the distal portion 108 of the catheter 100 need not be 6.1 mm but rather would be a function of the vessels into which it is to be inserted. In other applications currently contemplated, the outer diameter of the distal portion 108 could be about 4 mm to about 8 mm. More generally, the outer diameter can be within a range of about 2 to about 14 mm.

Additionally, as discussed below, the distal portion 108 preferably is formed to be relatively flexible. The flexibility permits the distal portion 108 to relatively gently interact with the blood vessel in which it resides. In one application, the catheter 100 is applied through a superficial vessel and is advanced through the internal jugular vein toward the heart. In this environment, a relatively low stiffness construction is sufficient for delivery of the distal portion 108 the catheter 100.

Figure 2A:
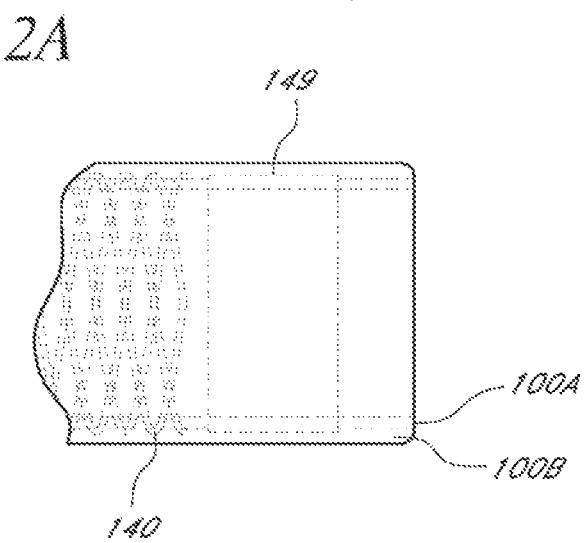
FIG. 2A is a schematic view of a distal portion of the catheter illustrating techniques for embedding a braided structure therein.

FIG. 2A illustrates one approach to making the catheter 100 more flexible in which a soft material is incorporated into the elongate body 112. In various embodiments, all or a portion of the elongate body 112 can be formed of any suitable flexible elastomer, such as polyurethane, CFlex, SIBS (styrene isoprene butadiene) or polyolephins. In one example, silicone tubing can be used in an inner portion 100A of the catheter 100. More generally, the elongate body 112 can be formed of an implantable thermoplastic elastomer. In one embodiment, silicone tubing has a durometer of about 50 Shore A or less is used to form the inner portion 100A of the catheter 100. In some applications, the catheter 100 can be formed of a material having a durometer of 30-80 Shore A will perform adequately. In other embodiments, a higher or lower durometer material can be used. As further discussed below, there can be particular advantages to the softer durometers of 30-60 Shore A and 40-50 Shore A. As discussed further below, an outer portion 100B of the catheter 100 can be formed of a similar or the same material as the inner portion 100A.

In addition, at least one of the outer and inner portions 100A, 100B can include hydrophilic or lubricious coatings. These coatings may provide improved performance. For example, such coatings can enhance performance such as improved lubricity for deployment and reduced thrombogenicity for improved patency. Also, for the temporary stent discussed below such coatings can help to facilitate explant procedures.

In various embodiments, the base material preferably is flexible and base material strength is less critical. In this application, the ability for the braided tubing to expand radially over a connector barbs is preferred. As mentioned previously this is an advantage of a braided reinforcement over a single filament, coiled reinforcement, which cannot expand to slip over a barb. This is similarly an advantage of braid reinforced tube using a softer base material (such as one with a relatively low durometer, e.g., <70 Shore A) over one with a harder base material. Forcing a braided tube with a hard base material over a barb would require an unacceptably high force. Furthermore, under the forces anticipated to be applied during in use, a braided tube with a harder base material would not provide the degree of necking that is desirable in some clinical situations.

The catheter 100 also can include a braided structure 140 or other reinforcing member between the inner portion 100A and the outer portion 100B. The braided structure 140 provides a number of benefits to the catheter 100. For example, the braided structure 140 can be configured to contribute to at least in part, resistance to radial compression of the elongate body 112. Also, the braided structure 140 can be configured to provide at least in part, resistance to kinking of the elongate body 112.

In one embodiment, the braided structure 140 is provided primarily to enhance the security of a connection between the catheter 100 and another component of a blood carrying system, such as the vascular access system 10. For example, the braided structure 140 can enhance the security of an engagement mechanism of which the braided structure forms a part.

In one embodiment, the braided structure 140 includes a proximal end 144 and a distal end 148. The braided structure 140 can be disposed about the lumen 120, e.g., substantially or completely surrounding the lumen. The braided structure 140 also can extend along the lumen 120 such that the proximal end 144 is within the proximal portion 104 of the elongate body 112 and the distal end 148 is within the distal portion 108 of the elongate body. In one embodiment, the braided structure 140 is configured such that the proximal end 144 extends to or adjacent to the proximal end of the elongate body 112.

In one embodiment, the braided structure 140 is configured such that the distal end 148 is located proximal of the distal end of the elongate body 112. For example, the distal end 148 of the braided structure 140 can be located about 0.2 inches, about 0.25 inches, or from about 0.2 to about 0.25 inches proximal of the distal end of the catheter 100. This arrangement permits a device for visualization to be located distal of the distal end 148 of the braided structure 140. For example, a radiopaque marker 149 can be located in the distal portion 108 of the elongate body. In one embodiment, the radiopaque marker 149 is a ring formed of platinum, tantalum, tungsten, gold, palladium, iridium, barium sulfate, or another radiopaque material, and any combination thereof. Although the marker 149 is configured as a solid ring, in other embodiments, these marking materials can be doped into layers of the catheter 100 or configured as a plurality of rings or one or more patches, plates, wire, or other shapes. They may be distributed in the entire device or at one or both ends of the device or anywhere in between. Any other suitable device to provide the clinician with an indication of where the distal portion 108 of the catheter 100 is located when the blood flow conduit is being advanced in the vasculature can be used instead of the radiopaque marker 149 as will be understood by those skilled in the art.

Also, the configuration of the braided structure 140 can be varied along the length of the catheter to optimize certain performance metrics of the catheter. For example, as discussed herein, the distal portion 108 preferably is relatively flexible to minimize trauma to the patient's vasculature. As discussed below, certain therapeutic methods benefit from higher hoop strength or outwardly directed force. It is thought to be advantageous to have high hoop (radial) strength while having low bending strength. This produces a device which is resistant to collapse but is flexible for accommodating various structures within the body while minimizing the force exerted by and upon the device. Where such properties are primarily derived from the braided structure, it may be desirable to enhance these properties by varying the braid pattern in a treatment zone. These variations can be achieved by varying the pic count of the braided structure 140. Additionally, a proximal portion of the braided structure 140 can be optimized to enhance the connection strength of an engagement mechanism as discussed herein.

FIG. 2A illustrates that the braided structure 140 can be embedded in the elongate body 112. In one embodiment, the braided structure 140 is embedded in the elongate body 112 such that an outer surface of the elongate body 112 surrounds the braided structure 140. In some cases, the braided structure 140 is disposed within the elongate body 112 such that the outer surface of the elongate body 112 is substantially smooth along the longitudinal axis of the catheter body. When embedded in the elongate body 112, the braided structure 140 also can be disposed radially outside of the inner wall 116 of the elongate body 112. The braided structure 140 also can be disposed radially between the inner wall 116 of the elongate body 112 and an outer surface thereof.

Although the catheter 100 is relatively soft, the braided structure 140 provides reinforcement that prevents or substantially minimizes kinking, crushing, and other phenomenon that can cause at least partial collapse of the lumen 120. Collapse of the lumen 120 can occur when the catheter 100 traverses a bend of relatively small radius. For example, in some applications the catheter 100 is required to traverse a joint, such as the shoulder of a patient. Such a traverse could require a relatively small bend radius. In other applications, the catheter 100 need not traverse a small bend radius (e.g., when not crossing a joint). In some applications, a preferred routing of the catheter 100 may cause the conduit to traverse a bend with a radius of about 1.0 inch. In some applications, a preferred routing of the catheter 100 may cause the conduit to traverse a bend with a radius of 1.0 inch or more. In other applications, in a preferred routing the catheter 100 may have to traverse a bend with a radius of about 0.25 inch. In other applications, in a preferred routing the catheter 100 may have to traverse a bend with a radius of about 0.5 inch. In other applications, in a preferred routing the catheter 100 may have to traverse a bend with a radius of between about 0.25 inch and about 1.0 inch. In all of these cases, the braided structure 140 provides a reinforcement to prevent or substantially minimize collapse of the lumen 120.

Properties of the braided structure 140 and variations thereof result in desirable kink minimizing properties not achievable using a coil reinforcement. At very small bend diameters, the braided structure 140 is expected to gradually flatten, instead of suddenly inflecting to a kinked configuration. This is advantageous for several reasons. First, gradual flattening of the braided structure 140 will be detectable by a clinician (e.g., using an imaging technology such as X-Ray imaging) such that the clinician can recognize that a less than desirable bend radius is present before full narrowing of the blood conduit occurs. Secondly, a coil reinforcement undergoes higher strain levels and alternating strains than the braided structure 140. This prevents or delays undesirable fracture or failure due to repeated flexure at very small bend radii. In addition, only a fraction of the plurality of members in the braided structure 140 undergo significant stress or strain level at minimum bend radii. The braid members on the top and bottom of the fold undergo negligible stress compared to the members at the sides of the fold. This means that even if the loading conditions were severe enough to fracture braid members on the sides of the fold, the majority of braid members at the fold would not fracture and the device would remain substantially intact. In previous single filament, coil reinforced devices, any fracture was potentially catastrophic. Also, the disclosed braid configurations advantageously exhibit full narrowing or kinking at a much smaller bend radii than prior coil reinforced devices. Prior coil reinforced devices had a kink radius of approximately 0.5 inch, whereas various embodiments of the catheter 100 have a kink radius of approximately 0.2 inches.

In some embodiments, the braided structure 140 forms a part of an engagement mechanism, similar to the engagement mechanism 32.

Figure 3:
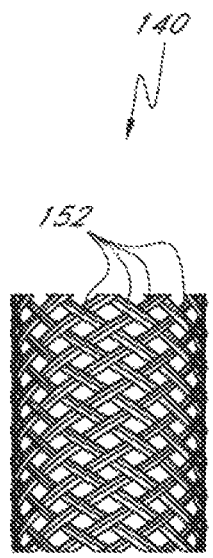
FIG. 3 is a side view of a reinforcement member configured to be incorporated into the blood flow conduit of FIG. 2.

FIG. 3 illustrates further details of one embodiment of the braided structure 140. In one embodiment, the braided structure 140 has a plurality of braid members 152 that overlap each other in the structure. The braided structure 140 can comprise a shape memory material, such as a nickel titanium alloy (e.g., a nitinol alloy) in various embodiments. Other suitable materials include stainless steel (e.g., 304 or 316), titanium, glass, Kevlar and other similar fibrous materials. For example, each of the braided members 152 can comprise a nickel titanium alloy or other shape memory material. In some embodiments, the braided members 152 are woven together to form the braided structure 140. The braid members 152 can have a cross-section with a first transverse dimension D1 being greater than a second transverse dimension D2, the first transverse dimension D1 being perpendicular to the second transverse dimension D2. In one embodiment, the second transverse dimension D2 (e.g., the shorter of the two dimensions) is generally radially extending relative to the longitudinal axis of the lumen 120. These embodiments are illustrated by FIG. 3A.

Such an arrangement can minimize the thickness of the elongate body 112 between the inner wall 116 and the outer surface of the elongate body. This can result in a very thin structure, e.g., with a thickness of about 2.0 mm or less. In one embodiment, the thickness of the catheter 100 between the inside wall 116 and an outer surface of the catheter is about 1.1 mm. In one embodiment, the thickness of the braided member 152 is less than about 50 percent of the thickness of the elongate body 112. In one embodiment, the thickness of the braided member 152 is less than about 25 percent of the thickness of the elongate body 112. In one embodiment, the thickness of the braided member 152 is about 10 percent of the thickness of the elongate body 112. Minimizing the thickness of the wall of the catheter is important in some embodiments because it can maximize the size of the lumen for carrying blood while still maintaining the ability to insert the catheter 100 into selected vessels.

By reducing the dimension D2, the crossing profile of the catheter 100 can be reduced or minimized. Reducing the crossing profile provides an advantage of permitting access to the vascular system through a smaller incision. In some embodiments, by reducing the dimension D2, the size of the lumen 120 can be increased for a given crossing profile. Increase in the size of the lumen 120 is advantageous in that it permits greater fluid carrying capacity in the lumen. The braided structure 140 provides considerable kink and crush resistance and relative flexibility of the elongate body 112.

Figure 3A:
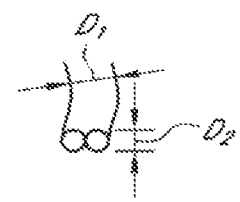
FIG. 3A is an end view of one braided member of the braided structure of FIG. 3.

One embodiment illustrated by FIG. 3A provides a plurality of braided members 152 that have elongate cross-sections provided by a plurality of axi-symmetric side-by-side wires. For example, a braided member could include two circular cross-section wires provided in a side-by-side arrangement. In this embodiment, the radial dimension (D2) of the braided members 152 is about equal to the diameter of the wires and the dimension transverse to the radial dimension (D1) is about equal to twice the diameter of the wires. One useful construct for the braided members 152 incorporates two 0.005 inch wires that are formed of a nickel titanium alloy. Other embodiments could incorporate 0.006 inch or larger wires. Some embodiments could incorporate 0.004 inch or smaller wires. Larger wires may be suitable for larger catheters or for catheters that can use smaller lumens. Smaller wires may be suitable for smaller catheters or for catheters subject to less crush or kink forces. In other embodiments, the braided members 152 can be formed with one or more flat or oval cross-section wires. A suitable alloy would include 56 weight % nickel and 44 weight % titanium. This material can be treated to provide suitable properties, such as by a straight annealing. A light oxide finish is suitable for some embodiments.

Any suitable woven pattern can be provided for creating the braided structure 140. For example, a hopsack weave can be employed in which the braided members 152 cross over a first transverse braided member then cross under a second transverse braided member adjacent the first transverse braided member. This pattern can be repeated throughout the braided structure 140 to provide a suitable weave. Hopsack weave is sometimes referred to as a diamond pattern full load. In other embodiments, the weave could be a diamond pattern half-load or a herringbone weave, which will be understood by one skilled in the art. Other weave arrangements that can be used include a linen weave, for example. However, for some applications, the linen weave is not expected to perform as well as other weave patterns discussed herein.

Further aspects of the braided structure 140 can affect its performance. For example, the density and configuration of the braided members 152 can affect the degree of security when the catheter 100 is engaged with another blood carrying component. For example, in one embodiment, the braided structure 140 is formed with a suitable helix angle, which is defined as the angel between any of the braided members 152 and a longitudinal axis of the braided structure 140. A helix angle within a range of about 40 degrees to about 65 degrees could be used in some embodiments of the braided structure 140. In other embodiments, the braided structure 140 can be formed with a helix angle in the range of about 50 degrees to about 55 degrees. In one embodiment the braided structure 140 defines a helix angle of about 51 degrees. In one embodiment the braided structure 140 defines a helix angel of about 54 degrees. A higher helix angle creates a more flexible catheter. A lower helix angle provides less flexibility but is easier to advance over a connector as discussed below. Lower helix angle also provides a less crush resistant catheter, which is less optimal in some applications.

Another aspect of the braided structure 140 that relates to the performance of the engagement mechanism 32 of which the braided structure may be a part is the pic count (crossings per unit length) of the braided structure 140. One skilled in the art will recognize that pic count and helix angle are related. More particularly, pic count can affect the connectability of the catheter 100 with a connector, which can form a part of the third blood carrying conduit 30. Greater pic count corresponds to a higher force required for coupling the engagement mechanism 32. Lesser pic count corresponds to lower connecting forces. Catheters with lower pic counts are more subject to kinking. In one embodiment, the braided structure 140 has a pic count between about 21 ppi and about 24 ppi. In another embodiment, the braided structure 140 has a pic count of between about 22-24 ppi when assembled on the catheter 100. In another embodiment, the braided structure 140 has a pic count of about 21 ppi. In another embodiment, the braided structure 140 has a pic count of about 23 ppi. In another embodiment, a pic count of 22 ppi would be suitable.

Figure 7:
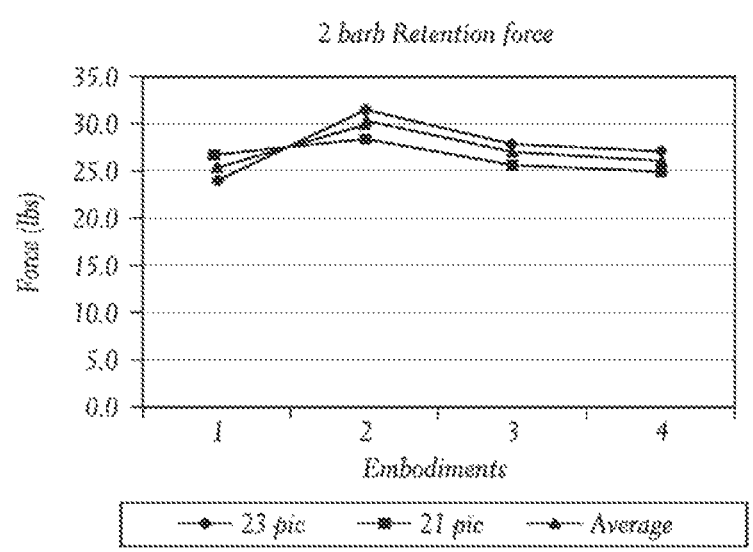
FIG. 7 is a graph illustrating a retention force for an engagement mechanism having a braided structure with different pic counts.
Figure 8:
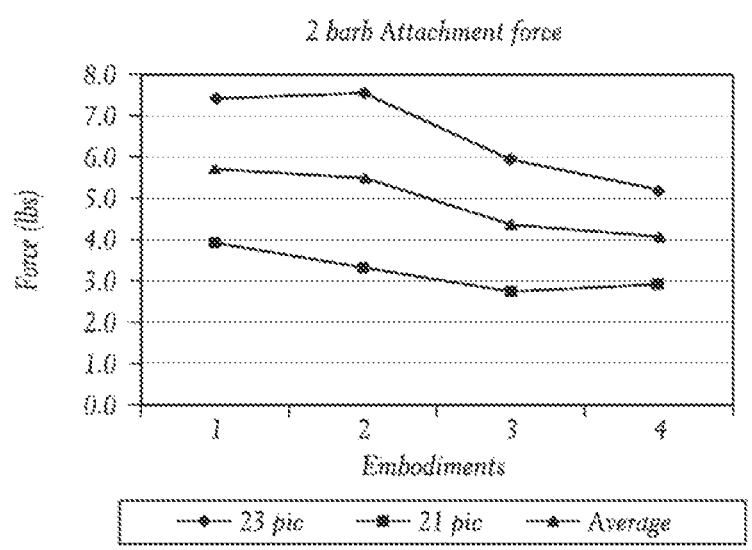
FIG. 8 is a graph of attachment forces for various embodiments.

FIGS. 7 and 8 illustrate a comparison of the retention force and attachment force respectively for various embodiments of an engagement mechanism. In this study, pic count of a braided structure in a catheter and various aspects of the engagement feature 240 of the connector 200 were varied. The variables that were varied in the connector 200 are shown in the table below, with all dimensions being in inches):

| | Length of Barb 244 | Length of Barb 248 | Spacing Between Barbs 244 and 248 | Height of barb 244 | Height of barb 248 |
| --- | --- | --- | --- | --- | --- |
| Embodiment 1 | 0.065 | 0.065 | 0.240 | 0.012 | 0.012 |
| Embodiment 2 | 0.065 | 0.05 | 0.225 | 0.012 | 0.011 |
| Embodiment 3 | 0.065 | 0.05 | 0.240 | 0.012 | 0.011 |
| Embodiment 4 | 0.065 | 0.04 | 0.240 | 0.012 | 0.009 |

FIG. 8 shows a general trend to lower attachment forces for Embodiment 4 compared to other embodiments. Embodiment 4 had lower values for the height and the length of the barb 248. Also, FIG. 8 shows that a lower pic count of the braided structure of the catheter can result in a significantly lower attachment force compared to a higher pic count arrangement, where the connector has two barbs. Lowering the attachment force is desirable in some embodiments to provide faster and easier assembling of a vascular access system in-situ for the clinician.

FIG. 7 shows that for the embodiments described in the table above, retention force (e.g., the force needed to disconnect the catheter 100 from the connector 200) was not highly dependent on pic count for the embodiments of the connector studied. Although there is an increase in retention force for Embodiment 2 compared to the other embodiments, all four embodiments had relatively high retention forces compared to an engagement mechanism including a connector with a single barb engaged with a catheter having a braided structure.

Also, the performance of the braided structure 140 can relate to the number of wires incorporated into the weave. In some embodiments, the braided structure 140 includes about forty-eight braided members 152. Other numbers of braided members 152 can be provided, however. For example, in one embodiment, twenty-four braided members 152 can be provided. Fewer wires provide less crush and kink resistance. More wires provide greater resistance in the braided structure 140 to kinking and crushing. Other numbers of wires for forming the braided structure 140 can also be used, as will be understood by one skilled in the art.

In some embodiments, the conduit 30, the connector 200, and variants thereof can be in the form of a connector and can be coupled with or integrated into another treatment device for handling blood. For example, the conduit 30 can comprise a connector for connecting a pump or other component of a vascular assist device or other cardiovascular treatment device. These combinations provide very secure connections between such components and the catheter 100 and variant thereof as discussed herein.

Techniques for Forming Blood Carrying Conduits

Various techniques are contemplated for forming the catheter 100 with inner and outer portions 100A, 100B. In some techniques, the outer portion 100B is formed in a different process than the inner portion 100A. For example, the in a first step of one embodiment, an elongate tubular section of silicone or a flexible elastomer is slid onto a solid mandrel to provide the inner portion 100A. The tubular section can have a durometer of about 50 shore A or any other suitable hardness as discussed herein. The tubular section optionally is loaded with barium sulphate. In one technique, the inner diameter of the tubular section is about 5.0 mm and the outer diameter of the tubular section is about 5.5 mm.

Thereafter, the braided structure 140 can be placed over the outer surface of the inner portion 100A. The braided structure 140 can have a diameter of about the same as that of the tubular section outer diameter. In one embodiment, the braided structure 140 has an inner diameter of about 5.5 mm. In one embodiment, the braided structure 140 has an inner diameter of slightly less than the outer diameter of the tubular section. For example, an inner diameter of about 5.4 mm for the braided structure 140 would be suitable. This arrangement causes the braided structure 140 to cinch down on the outer surface of the tubular section forming the inner portion 100A. In one technique, the braided structure 140 is sized such that its length is substantially the same as or slightly less than that of the tubular section.

Thereafter a platinum iridium marker band (or visualization device of other configuration) is positioned over the inner portion 100A. This can be achieved by sliding the marker band over the distal end to a location between the distal end of the braided structure and the distal end of the tubular section. In another technique, strands of the braided structure 140, particularly strands located in the distal portion thereof, can be configured to be visible using radiography or another similar technique.

Thereafter, the assembly formed to this point in the process can be covered with a suitable material to form the outer portion 100B of the catheter 100. For example, the assembly can be coated with a suitable material to form the outer portion 100B of the catheter 100. In one technique, the outer portion 100B is formed by dip or spray coating silicone, polyurethane or other suitable material over the assembly. In another technique, the outer layer can placed over the assembly and bonded, shrunk, thermally fused or otherwise formed together. In another technique, the outer layer can be formed by in-line extrusion over the assembly.

Other optional steps can thereafter be performed in various embodiments. For example, the construct can be cut to size and luer fittings (or other suitable connectors) can be formed on a proximal end thereof as needed. The forgoing steps are illustrative and need not be performed in the order recited.

Engagement Features & Mechanisms

As discussed above, in various embodiments, the braided structure 140 extends to the proximal portion 108 of the catheter 100. At least the portion of the braided structure 140 that so extends can interface with the blood carrying conduit 30 forming a part of the engagement mechanism 32.

Figure 4:
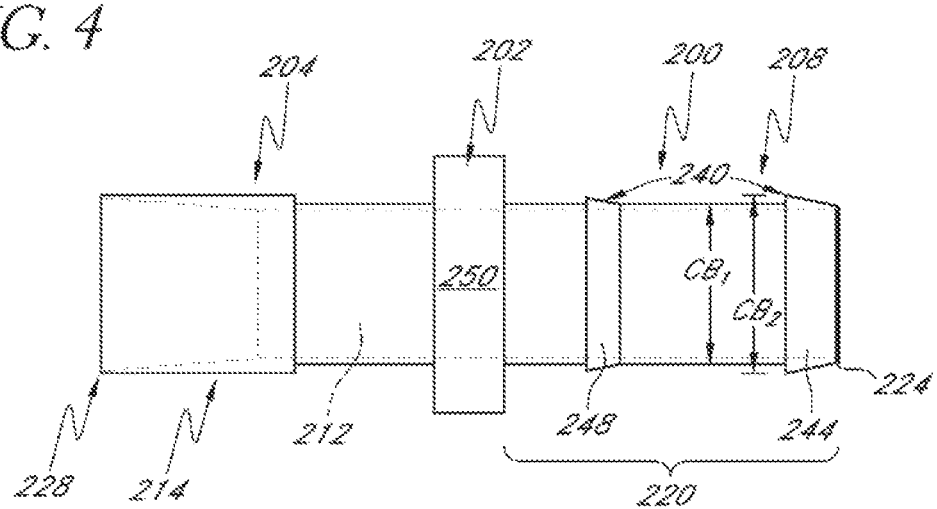
FIG. 4 is a plan view of a connector that is adapted to couple a first blood flow conduit with a second blood flow conduit.

FIG. 4 illustrates one embodiment of a connector 200 that can be incorporated into the blood carrying conduit 30 of the system 10. The connector 200 includes a connector body 202 that has a proximal portion 204, a distal portion 208, and lumen 212 extending therebetween. The lumen 212 can take any suitable form. In one embodiment, the lumen 212 includes a tapered section similar to that described in U.S. application Ser. No. 10/962,200.

The proximal portion 204 preferably is configured to interface with, e.g., be coupled to, the blood carrying conduit 22. The connection between the connector 200 and the conduit 22 can be achieved in any suitable manner. For example, the proximal portion 204 can have an enlarged portion 214 over which the conduit 22 can be advanced. The enlarged portion 214 can comprise a portion of the engagement mechanism 36. Other techniques and structures for connecting the connector 200 and the conduit 22 are described in the applications incorporated by reference herein above, including U.S. application Ser. Nos. 11/216,536 and 11/600,589.

The distal portion 208 is configured to interface with the blood carrying conduit 26 or with the catheter 100. In one embodiment, the distal portion 208 includes an outer surface 220 that extends between a distal end 224 and a proximal end 228 of the connector 200. In one embodiment, the outer surface 220 extends from the distal end 224 to a proximal end of the distal portion 208, adjacent to an enlarged segment 250. The connector 200 also includes an engagement feature 240 that is disposed on the outer surface 220. In one embodiment, the engagement feature 240 comprises a portion of an engagement mechanism.

The engagement feature 240 can take any suitable form. For example, in one embodiment, the connector body 202 has a first outer size $CB_1$ and the engagement feature 240 has a second outer size $CB_2$ that is greater than the first outer size $CB_1$. The outer sizes $CB_1$, $CB_2$ can correspond to diameters in one embodiment, but could correspond to outer perimeters. In one embodiment, $CB_1$ is a diameter of about 5.4 mm. In one embodiment, $CB_2$ is a diameter of about 6.0 mm. As discussed above, the inner diameter of the catheter 100 is about 5.0 mm in one embodiment. This corresponds to a prestressing of about 1 mm in the diameter of the catheter 100. In some embodiments, a prestressing of about 20% of the inner diameter of a catheter being inserted over the engagement feature 240 can provide suitable connectability. In some embodiments, a suitable amount of prestressing (e.g. enlargement of the inner diameter of a catheter connected over the engagement feature 240) can range from 16-24%. In other embodiments, a suitable amount of prestressing (e.g. enlargement of the inner diameter of a catheter connected over the engagement feature 240) can range from 8-28%.

Prestressing, or stretching the inner size of the catheter 100 creates an enhanced security of the connection formed by the engagement mechanism 32. In particular, the braided structure 140 and the proximal portion of the catheter 100 expand upon being placed in compression during the distal advancement of the connector 200 relative to the catheter. After advancement, the braided structure 140 seeks to return to its pre-formed shape, which produced an inwardly directed force on the connector 200 increasing the security of the engagement between the connector 200 and the catheter 100. Also, the configuration of the braided structure 140 is such that if a force for disconnecting the connector 200 and the catheter 100 is applied, the braided structure will increase the inwardly directed force further securing the connection. This action at the engagement mechanism is analogous to a Chinese finger trap toy, which reduces in cross-sectional size upon elongation.

Providing one or more barbs creates an even more secure connection. In some embodiments, the engagement feature 240 includes a barb 244 that extends over a portion of the connector body 202. The barb 244 can include any structure that includes a raised surface that extends to above the connector body.

FIG. 4 illustrates that in one embodiment a second barb 248 is provided between the first barb 244 and the proximal portion 204 of the connector 200. As discussed below, the second barb 248 of the engagement feature greatly enhances the security of the connection between the catheter 100 and the connector 200. The second barb 248 can take any suitable form. In some embodiments of the connector 200, the second barb 248 is smaller than the first barb 244. For example, the second barb 248 can be about 5.8 mm in diameter in one embodiment. The first barb 244 can be about 5.99 in diameter.

In some embodiments, the height of the engagement feature 240 (e.g., the barbs 244 or 248) can be important. Barb height can be measured on the distance from a location of the barb that is farthest radially from an axis of the lumen through the connector 200 to the surface 220 adjacent to the barb 244, 248. In one embodiment, this distance is between about 0.005 inches and about 0.020 inches. In one embodiment, the height of the engagement feature is about 0.013 inches. In one embodiment, the height of the engagement feature is about 0.012 inches. In one embodiment, the height of the engagement feature or barb is between about 0.008 inches and about 0.009 inches. In one embodiment, the height of a first barb of the engagement feature 240 is about 0.012 inches and the height of a second barb of the engagement feature 240 is about 0.008 inches. The height and diameter of the engagement features 240 can be increased to increase retention force. In some embodiments, increasing these dimensions may be limited by the force required to advance the connector 200 into the catheter 100, which is generally done manually.

Another aspect of the engagement feature 240 is the length thereof or of individual portions thereof. For example, one embodiment has two barbs as discussed above. In one arrangement a distal-most barb is about 0.065 inches in length, though longer barbs could be used. In one embodiment, a proximal-most barb is about 0.065 inches in length. The proximal-most barb can be shorter or longer. For example, in one embodiment, the proximal-most barb is about 0.040 inches in length. In one embodiment, the distal-most barb is 0.065 inches and the proximal most barb is 0.040 inches.

Two additional features that contribute to the connection in some embodiments are the spacing between the barbs 244, 248 and the distance that the catheter is advanced past the proximal most barb.

Figure 5:
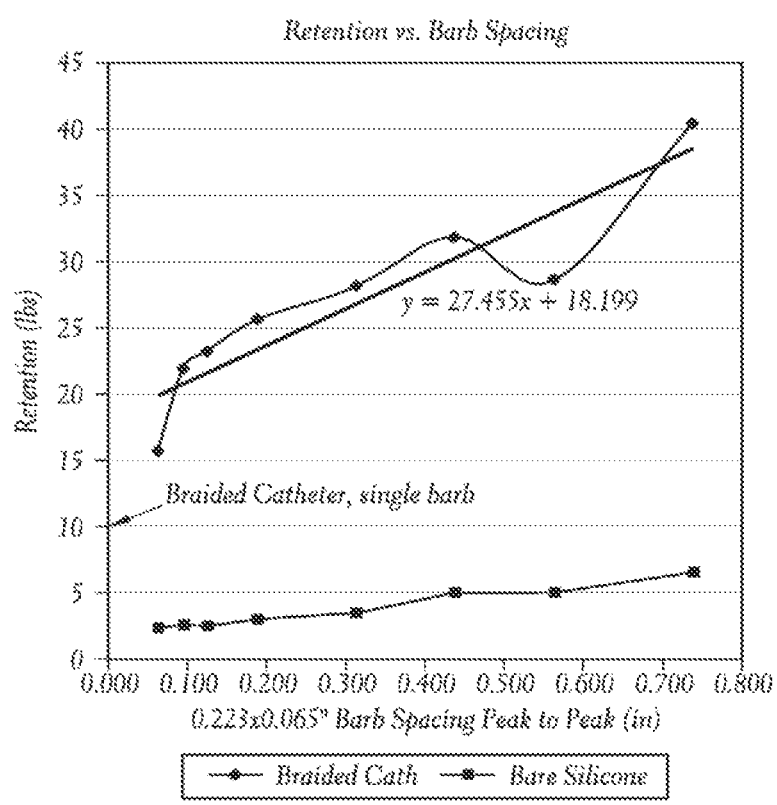
FIG. 5 is a graph illustrating a retention force for various engagement mechanisms described herein.

FIG. 5 demonstrates performance of various barb spacings. One configuration was tested with a maximum peak to peak barb spacing of about 0.740 inches. This chart shows a general trend of increase in retention force for greater barb spacing. Some of the increase in force observed in the chart could be attributable to a greater length of catheter in contact with the connector apparatus. As the barb spacing increased, so did the total length of connected catheter. FIG. 5 can be interpreted to indicate a minimum spacing of approximately 0.100 inches in some embodiments. At lesser barb spacings than this value the retention force drops rapidly. However, at increased spacings greater that this value, the force increases more slowly. In FIG. 5, one technique computed the rates of change as about 7 lbs/0.040 inches before an inflection point and about 1.2 lbs/0.040 inches after the critical point. This analysis employed a simple linear fit. One skilled in the art will recognize that a more complex fit of the data would produce a different mathematical description of the data. However, it is expected that other such curve fits would still reveal a relatively steep slope toward 0.100 inches and a flatter slope toward the middle of the data. Similarly in FIG. 6, discussed below, a more complex curve fit might reveal a generally asymptotic profile at one or both ends of the data set.

FIG. 5 shows that the dual barb configuration has superior connection strength to a single barb at all barb spacings and more than twice the strength once the peak to peak spacing exceeds about 0.100 inches. Also, the difference between bare silicone and braid reinforced silicone is apparent in FIG. 5. Note that in addition to the superior performance at any barb spacing, the slope of the line is greater for a braided catheter. This may be due in part to an amplified retention force generated by the combination of the retention feature 240 and the braided structure 140 in the catheter 100 upon connection of the catheter to the connector 200. This highlights the superiority of the braided flexible catheter over alternative designs. More particularly, the braided structure has much greater retention strength for a given barb dimension compared to a non-braided catheter of identical material. Also, the braided structure has the ability to further increase the retention strength by the use of multiple barbs on the connector 200. Also, the use of the braided structure compared to other reinforcements facilitates the use of barbs and optimized barb geometry on the connector 200. Moreover, the use of a soft elongate body 112 in the catheter 100 allows the braided structure 140 to neck down behind the barb and thereby increase the retention strength.

Given the results illustrated in FIG. 5, the spacing can be any suitable spacing, but as discussed below preferably is at least about 0.100 inches in an arrangement with two barb, or more. In one embodiment, the spacing between the peaks of adjacent barbs 244, 248 is about 0.229 inches. In one embodiment, the spacing between the peaks is about 0.240 inches.

Although FIG. 5 illustrates the vast improvements that can be achieved with the embodiments described above, in some applications an engagement mechanism having less redundancy provides adequate retention force. For example, FIG. 5 shows one embodiment where an engagement mechanism with a single barb provides about 10 pounds of retention force. This amount of force is sufficient for some applications. Also, although FIG. 5 shows that bare silicone generally provides a much lower retention force for various dual barb arrangements a combination of bare silicon and a connector can be sufficient in some arrangements, such as if the silicone is clamped at an outside surface thereof.

Figure 6:
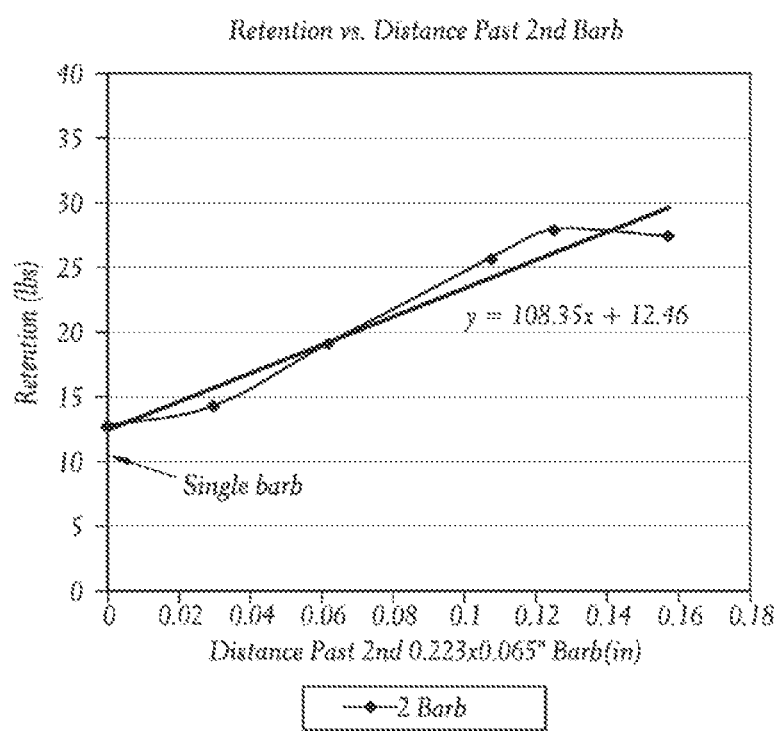
FIG. 6 is a graph illustrating a retention force corresponding to various techniques for connecting an engagement mechanism having two barbs.

In various embodiments, it is preferable to advance the catheter proximally past the proximal-most barb. The sensitivity to this variable is illustrated by FIG. 6. Also, a single barb example is illustrated in FIG. 6. The dual barb variable setup demonstrated little or no increase in retention force when the amount past the barb exceeded about 0.125 inches for one embodiment. This suggests that a suitable range for the catheter connection past the barb could be about 2-3 mm (0.080"-0.120") or about 1.5-4 mm (0.060"-0.160") for one embodiment of the catheter and connector combination.

FIG. 6 shows that a catheter flush with the proximal side of the second barb exceeds the retention strength of a single barb where the catheter is about 0.125 inch or less beyond the proximal side of the single barb. Other embodiments provide advancement beyond the retention feature 240 of between about 0.080 inches and 0.120 inches. In some embodiments, it is preferable to advance the catheter proximally past the proximal-most barb by between about 0.060 inches and 0.160 inches. In some embodiments, it is preferable to advance the catheter proximally past the proximal-most barb by about 0.010 or about 0.111 inches. In some embodiments, it is preferable to advance the catheter proximally past the proximal-most barb by between at least about 0.125 inches.

As discussed above, the engagement mechanism 32 particularly when configured to include portions of the catheter 100 and the connector 200 provides a number of clinical advantages over other arteriovenous shunt devices. Specifically, the combination of at least one of a braided structure and a barb in the engagement mechanism improves the ease of use of the device. As discussed above, the catheter 100 can be cut and connected without the need to further modify a catheter prior to connection. Also, the embodiments discussed herein have improved connectability in that a lesser force can be used to connect the engagement mechanism 32 than would be sufficient to disconnect the mechanism. Also, the system 10 is "one-size-fits-all" because it is configured to be trimmed to any desired length.

Other advantages that are provided include improved durability. The catheter 100 has many independent braided members 152 within the braided structure 140. The plurality of braided members 152 provides redundant support, which results in improved resistance to clamping and fatigue fracture. The plurality of braided members 152 also provides improvement in tensile strength. Compared to other prior approaches, less manufacturing steps are required, reducing the labor and cost of production. Also, it is expected that at least some of the embodiments of the catheter 100 withstand higher radial loads before collapsing and can be placed in a tighter radius without kinking than was possible with prior devices. In at least some applications, improved burst resistance (the ability to withstand high pressures without detaching from the connector or rupturing) can be advantageous but is not required.

Other advantages of the embodiments discussed herein include a benefit for the physician to receive feedback indicating that the catheter has been properly connected. For example, the multiple barb system provides increase in strength even when the catheter is minimally past a second barb. Visible deformation, e.g., by expansion of the catheter 100 or the braided structure 140, serves as a visual indication of proper attachment. This allows the user to observe the visible reference to insure that the catheter is past both barbs by referencing the two visible rings as the braided catheter goes over the first and second barbs. If not visible, this expansion can create ribbed portion on the otherwise smooth outer surface of the catheter 100 to provide a tactile confirmation of proper attachment.

Although it is recommended that the catheter be fully advanced against the central enlarged segment 250 of the connector 200, the integrity of the connection provides sufficient strength if inserted less than this amount, e.g., by only one-half of the distance from the barb 248 to the segment 250. This is expected to result in strength that is almost double when compared to a similar single barb system. When fully inserted it is expected that the strength will be almost tripled.

As discussed above, multiple and single barb engagement features can be suitable for secure connections. A properly designed single barb and braided catheter connection system can be made very secure, e.g., with about six times the retention force as a catheter made from the same material but without the braid. The second barb is expected to add at least a 100% increase in retention strength. This makes the engagement mechanism more robust, providing the added benefit of reducing the urgency of optimal insertion of the catheter over the connector to the enlarged section 250.

These features provide the desired level of security while providing the end user with both an increase in the confidence of achieving a secure connection.

Systems and Methods Adapted for Treating Vascular Stenosis

FIGS. 9-11 illustrate various methods and apparatuses for treating vascular stenoses. In each figure, a stenosis 300 is illustrated as narrowing the blood flow lumen of a vessel V compared to the un-occluded state of the vessel. The narrowing prevents blood from reaching tissue downstream, causing ischemia, insufficient blood flow for effective dialysis, and other maladies.

FIG. 9 shows, in an upper portion, a segment of the vessel V prior to being treated and, in a lower portion, the same vessel segment during a treatment with a temporary stent 400. The stent 400 is one form of a blood carrying conduit, as discussed herein and can incorporate certain structural features discussed above. In use, the stent 400 is placed in a blood vessel to displace the stenosis 300 to increase the blood carrying capacity of the vessel V, providing a method for opening up the vessel V. The stent 400 has a structure that causes it to move the stenosis 300 radially away from the center of the vessel V so that the vessel is wider. In contrast to known stents, the stent 400 is configured for temporary placement and remodeling of the vessel.

The stent 400 includes an elongate tubular member 404 having an outside surface that is configured to prevent adherence of in vivo matter. For example, it is preferred that the outside surface of the stent 400 prevents growth of tissue into at least a portion of the stent 400. For example, the outside surface can be formed similar to the outer portion 100B of the catheter 100, e.g., being formed of silicone or other silastic material. Alternatively, polymeric materials including polyerethanes with trade names such as Pellathane, Tecothane (aliphatic polyether polyurethane), Tecoflex (aromatic thermoplastic polyurethane) may be used. This is distinct from typical stents, which are configured as an open lattice or exposed cell pattern, though which tissue can easily grow. Because there is a preference to remove the device after a therapeutic period, such ingrowth is to be avoided. In some cases, the outer surface of the stent 400 also prevents cellular structures from the patient from adhering to the stent 400. Adherence of smooth muscle cells to the stent 400, which could impede removal of the stent, is resisted.

The tubular member 404 comprises a proximal end 408 and a distal end 412 and is reinforced to maintain an expanded configuration under a transverse load. Any reinforcement can be used, so long as the stent 400 has sufficient strength to displace the stenosis 300 and to produce a remodeling effect, as discussed herein. One reinforcement that is particularly useful is a braided structure. The braided structure 140 and any of its variants or substitutes discussed above can be used as the reinforcement.

The ability to displace the tissue surrounding a vessel to be treated depends on several factors, including the expanded size of the stent 400. In general, the unconstrained expanded width of the stent 400 should be greater than the stenosed vessel lumen width. If the stent 400 is generally self-expanding, it can relax from the stressed, reduced diameter size to a larger size, e.g., toward the unconstrained size. As discussed herein, the process of returning to the expanded size can be controlled as part of the treatment. In various applications, the unconstrained width (e.g., diameter) of the stent 400 can be about 4 mm to about 8 mm for certain vessels. More generally, the outer diameter can be within a range of about 2 to about 14 mm.

The length between the proximal and distal ends 408, 412 can be any suitable length. In some embodiments, the length is pre-determined. In other embodiments, the length of the stent 400 can be determined during the procedure. For example, the stent 400 can be formed during the procedure by cutting a portion of the tubular member 404 to create a selected size. The length can also be a function of the vasculature to be treated. For example, if the stent 400 is to be used to treat the neuro-vasculature, the length can be between about 2 cm and about 4 cm. If used to treat the carotid vasculature, the stent 400 can be between about 2 and about 15 cm. If used to treat peripheral vessels, the stent 400 could be longer.

One class of vessels for which the stent 400 may be particularly suited includes those vessels that are very mobile and subjected to high cycles, e.g., vessels traversing from one side to another of a skeletal joint. For example, the superficial femoral artery (SFA) traverses the knee joint and is cycled with every bend of the kneed. This subjects the SFA to tremendous movement and any structure in it to corresponding cycles. The stent 400 has an extremely robust design to resist failure from fatigue induced by these cycles. For this reason, the stent 400 is believed to be advantageous for the SFA and similar blood vessels. Typical lengths for SFA embodiments are between 40 mm and 550 mm. In certain embodiments, the stent 400 is configured to have a deployed length of between 200 and 300 mm. One embodiment is about 240 mm in length. In certain embodiments, the stent 400 is sized to be at least about twice as long as a typical lesion. Lesions are typically in the range of about 70 mm to about 100 mm. Other applications for the stent 400 include deployment in the biliary system and for such an application, the stent 400 would be sized appropriately to at least cover the stenosis and to be sufficiently large to dilate the lumen.

Other vessels in which the stent 400 could be deployed include the subclavian artery or vein, the internal jugular artery or vein, and inominate artery or vein, the superior vena cava.

In one method, the tubular member 404 is advanced into the vasculature of a patient in a low crossing-profile configuration such that the distal end 412 is disposed distal of the stenosis 300 and the proximal end 408 is disposed proximal of the stenosis 300. The low crossing-profile configuration can be induced by an axial load, such as a force applied to stretch or elongate the member 404. The axial load on the tubular member 404 is thereafter released to cause the tubular member to transition from the low crossing-profile configuration to the expanded configuration.

Figure 9A:
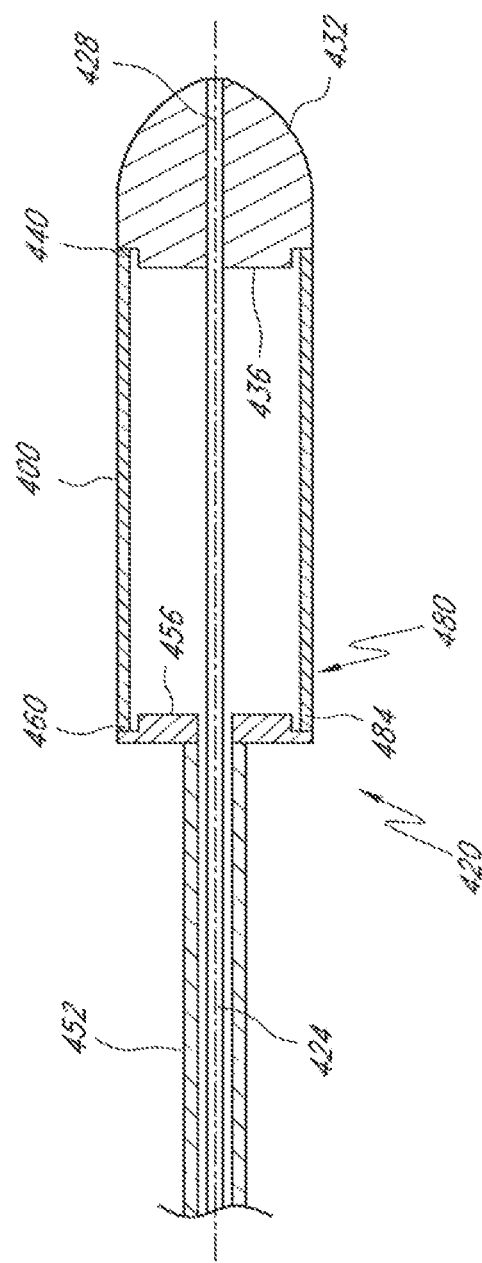
FIG. 9A illustrates a distal portion of one embodiment of a delivery device capable of delivering a temporary stent for a body conduit.

FIG. 9A illustrates a delivery tool 420 that is configured to stretch, and thereby to diametrically collapse, the stent 400. As the stent 400 is stretched, the diameter is reduced. The reduced diameter state enables the stent 400 to be advanced through a smaller incision and into smaller vessels. The delivery tool 420 includes a central elongate body 424 with a guidewire channel 428 extending therethrough. An atraumatic tip 432 disposed on a distal end of the elongate body 424 aids in tracking the tool 420 over the guidewire. A proximal portion 436 of the tip 432 has a stent engagement feature 440 adapted to grip at least one of a distal face of the distal end 412 of the stent or a circumferential band of the inner lumen of the stent 400 (similar to the inner lumen 120, discussed above).

A sleeve 452 disposed about the elongate body 424 is configured to be movable relative to the elongate body 424 and to provide the stretching function by such movement. For example, a distal portion 456 of the sleeve 452 can include a stent engagement feature 460 adapted to grip at least one of a proximal face of the proximal end 408 of the stent 400 or a circumferential band of the inner lumen of the stent 400 (similar to the inner lumen 120, discussed above).

In one deployment technique, the stent engagement features 440, 460 are coupled with the proximal and distal ends 408, 412 of the stent 400 respectively. Thereafter, relative motion is provided between the sleeve 452 and the elongate body 424 such that the stent engagement features 440, 460 are moved away from each other along the longitudinal axis of the tool 420. The movement causes the stent 400 to stretch, which reduces its diameter. The stent is thus moved to a low crossing-profile configuration.

After the stent 400 has been delivered to a treatment site, the axial load on the stent 400 is released to cause the stent 400 to transition from the low crossing-profile configuration to the expanded configuration. In one technique, the axial load of the tool 420 can be released by providing relative movement between the sleeve 452 and the elongate body 424 such that the stent engagement features 440, 460 are moved toward each other along the longitudinal axis of the tool 420. This causes the stent 400 to expand diametrically such that it separates from the tool 420. Preferably the depth of the stent engagement features 440, 460 is sufficiently small, e.g., sized with diameters similar to the diameter of the low crossing profile diameter, such that the elongate body 424 can be refracted through the lumen of the stent 400 and out of the patient after the stent is deployed. A variation of the tool 420 is to provide features 440 and 460 made of flexible material, e.g., silicone to provide the ability to collapse radially as the elongate body 424 is retracted.

A variation of the tool 420 provides a biasing force to bias apart prior to delivery stent engagement features. The biasing force can be released by an elongate wire or rip cord that is threaded through a channel of the tool 420. Releasing the biasing force releases the stretching function and allows for deployment of the stent 400. The stent 400 may be attached to one end of the tool 420 for transport to the treatment site as illustrated in FIG. 9A or contained within a delivery tool, such as between the tool 420 and a sleeve disposed over the tool 420.

A variation on the deployment tool 420 would maintain the compressed state of the stent 400 for example by providing a sheath disposed about the stent, with the stent in a collapsed state. The stent 400 can be placed in a collapsed state by folding at least a portion of the tubular member 404 inwardly into the lumen of the body. For example, an arcuate segment of the tubular member 404 can be involuted into the lumen and the ends of the segment can be brought together to create a smaller cross-sectional profile. A sleeve can be disposed about the inwardly folded stent. In one variation of this approach, a removable constraint is provided about the folded stent 400 to decrease the pressure applied by the stent 400 to the sleeve. This structure reduces the force needed to retract the sleeve compared to where the sleeve provides the entire compressive action to hold the stent 400 in the folded state.

An alternative to the deployment tool of FIG. 9A is a catheter device that deploys the stent 400 at approximately its full size. Such a deployment technique may be combined with other techniques or devices, such as distal protection devices that address the risk of side effects such as the dislodgement of plaque or thrombus.

Although inserting the stent 400 percutaneously would be advantageous, the significant clinical benefit of the stent 400 can be obtained even if the stent is placed by surgical cut down. For certain vessels that are relatively peripheral and superficial, such an approach may be preferred to a percutaneous approach.

Various treatments involve removing the stent 400 after a therapeutic period. In other words, the tubular member is intended to be a temporary implanted structure. This method can be applied anywhere in the vasculature, but is has been observed to work in the venous vasculature. The vessel was shown to have greatly improved patency compared to prior to the implantation of the device. The therapeutic period can be as few as 1 day. In some cases, the therapeutic period can be up to 12 months. Significant permanent benefit may take approximately 2 months.

In one variation, the stent 400 is configured to expand during a significant portion of the therapeutic period. This feature provides that upon deployment, the stent 400 is released to a first expanded diameter. After deployment, the stent 400 continues to expand to ever increasing diameters over time as the stenosis is moved and the vessel reacts to the force applied by the stent 400. The stent 400 may be constructed such that the radial force it exerts on the vessel or body conduit is low enough that the stent does not immediately expand to its fully unconstrained outer diameter (e.g., pre-deployment diameter). This configuration advantageously enables imaging techniques, such as X-ray or fluoroscopy, to be used to assess diameter change of the vessel over time. This diameter change can be used to determine the amount of force the vessel is exerting on the device. In one therapy, the stent 400 is monitored until an increase in size of up to about 100% of the delivery diameter is achieved. In another therapy, the stent 400 is monitored until an increase in size of at least about 50% of the delivery diameter is achieved. After these percentages increases, the stent 400 can be removed. This information can be used to predict the amount of vessel relaxation (vessel re-narrowing) upon removal of the stent. Accordingly, the stent 400 can be deployed for a therapeutic period that can be tailored to the needs of the specific patient and treatment to provide the proper amount of time to expand/remodel the vessel to the appropriate diameter. Another approach is to determine the therapeutic period by reference to a potential for vessel recoil. For example, where some recoil is anticipated, the expansion of the stent 400 can be monitored until the internal lumen in the stent 400 has a width (e.g., diameter) that exceeds the desired blood vessel bore by a predetermined amount. For example, the stent 400 can be monitored until its inner diameter is at least about 20% to 30% greater than the desired post-treatment bore of the vessel. In some techniques, the expansion of the stent 400 is greater than the desired post-treatment bore of the vessel by up to 20%.

One way to configure the stent 400 to provide this time-expansion property is to modify, e.g., lower the pic count of the braid 140 or otherwise reduce the radial stiffness to enhance the expansion range. Alternatively a smaller diameter braid wire or material with a lower modulus of elasticity may be used to reduce the stiffness. A lower pic count braid would result in a device that is more responsive, with more diameter change in response to changes in vessel loading.

The stent 400 preferably is configured to holds its position in the vessel V so that the treatment continues for as long as desired at the stenosis 300. Under the right conditions, friction may be enough to maintain the position of the stent 400 in the vessel. An additional outer material, outward flared ends or coarser surface texture may be employed to improve the friction between the stent 400 and the vessel wall.

Other techniques include using a fastener, such as a suture or clip, to affix the stent 400 in position. In other embodiments, it may be acceptable to provide a cuff, short length of endothelialization promoting structure, or a radially outwardly oriented barb at one or both of the proximal and distal ends 408, 412 of the elongate body 404.

FIG. 9A shows that in one embodiment a separation zone 480 is provided between a cuff 484 and the stent 400 to facilitate separation of the stent from the cuff 484. The separation zone 480 provides a partial, or relatively easily torn, bond between the stent 400 and the cuff 484. In this embodiment, ingrowth is permitted in the cuff 484 to stabilize the stent 400 and minimally invasive removability is provided. In the illustrated embodiment, the cuff 484 is disposed on the proximal end of the stent 400. This enables the leading edge of the stent 400 to be anchored when the stent 400 is deployed in a vessel where the blood flows through the lumen of the stent 400 in a proximal-to-distal direction. In other embodiments, the cuff 484 can be on the distal end of the stent, which may be beneficial for deployment in a vessel where the flow of blood is through the lumen in a distal-to-proximal direction. In other embodiments, cuffs may be provided on both the proximal and distal ends of the stent 400.

The cuff 484 could be constructed of a relatively soft, textile like construction having similar or less stiffness than the vessel wall. For example a ring of ePTFE or Dacron could be incorporated into the cuff 484. The cuff 484 can be very thin, in one embodiment about 0.010" thick, and in other embodiments between about 0.005 and about 0.015" thick. In other embodiments, the cuff 484 can be about 0.001" to less than about 0.005" thick. In some cases, the cuff 484 can be greater than 0.015" thick. The cuff 484 can be relatively short, for example about 0.100". In some cases, the cuff 484 can be between about 0.050" to about 0.500" long. In further embodiments, the cuff 484 can be less than about 0.050" long while in other embodiments, the cuff can be greater than 0.500" long.

The cuff 484 can be joined to the stent 400 by any suitable technique, such as by having a smaller internal diameter than the stent outer diameter or by an appropriately weak adhesive. Additionally, the cuff 484 could be constructed of a bioresorbable material to facilitate the return to totally native structures. The cuff(s) 484 can be configured to be fully encapsulated in the intima of the vessel or absorbed or dissolved into the blood over time.

When explant is desired, the stent 400 can be grasped and separated from the cuff(s) 484, which is left in place proximal and/or distal of the treatment zone. Separation from the cuff(s) 484 may be accomplished by applying a force to the stent 400 along the longitudinal axis of the blood vessel away from a cuff 484. For example, a balloon could be inserted into the lumen of the stent 400 and expanded into engagement with the inner wall of the stent 400. The inner wall of the stent 400 can be similar to the inner wall 116, discussed above in connection with the elongate body 112. A distal zone of the inner wall can be configured to have enhanced frictional engagement with an outside surface of an explant tool, e.g., with an outside surface of a balloon of an explant tool.

In various embodiments, the stent 400 is configured to make explant easier. As discussed above, the outer surface is configured to prevent or minimize adherence of in-vivo matter. In addition, the outer surface preferably is configured to slide very easily during explant, e.g., proximally out of a treatment zone. In one embodiment, silicone disposed at the outer surface of the stent 400 greatly reduced the proximal directed force needed to extract the stent 400 from the body. This low force slideability reduces the chance of any trauma to the treatment zone, which can cause bleeding, inflammation and potentially restenosis. Other materials can be provided on the stent 400 consistent with this. For example, inner layers or structures could comprise materials that would require higher force slideability than the outer layer. In some embodiments, an outer layer can comprise a hydrophilic coating, which can reduce the force needed to remove the stent 400, e.g., by increasing the lubricity of the stent 400. Other materials, such as those discussed above in connection with the catheter 100, with comparable low force slideability could be used to form the stent 400 or be disposed on the outer surface thereof.

As an alternative, a currently marketed intravascular snare may be utilized for retrieval.

FIG. 10 illustrates a treatment that can involve bypassing a stenosis using a blood circuit that is at least partially extravascular in nature. The method can also involve treatment of multiple medical maladies. For example, the method provides a bypass of a stenosis and provides vascular access for a periodic therapeutic procedure, such as hemodialysis.

Prior to the method, an occlusion 300 is noted in an artery or vein. The occlusion 300 results in a narrowing of the vessel V compared to, for example, an upstream segment A. This method can be performed with a catheter system 10A, as discussed above. A distal blood conduit 26A and a proximal blood conduit, which can include the conduit 22 and the conduit 30 are provided. As discussed above, the conduit 22 can be a graft made of a convention a material such as ePTFE. The conduit 30 can be a connector, such as the connector 200 illustrated in FIG. 4.

The connector 30, 200 preferably has one or more a retention feature located thereon, which can be similar to the barbs 244, 248, discussed above. The distal blood conduit 26A can be configured as a catheter 100' similar to the catheter 100 discussed above, e.g., having a braided structure 140 embedded therein.

A distal zone or portion 500 of the distal blood conduit 26A, 100' is inserted into the vasculature and through a stenosis in the vasculature. The distal portion 500 has at least two discrete regions in one technique. A first region 500A extends from the site of vascular access into the vessel V near the distal end of the un-occluded up-stream segment A. A second region 500B extends proximally from the distal end of the distal blood conduit 26A, 100'. The second region 500B is configured for soft interactions with the vasculature, as discussed above. This prevents any adverse side effects due to the presence of the second region 500B in the vessel.

The first region 500A preferably is optimized to treat the stenosis 300. In particular, the first region 500A can be sized, as discussed above in connection with the stent 400, to displace the stenosis 300 out of the lumen of the blood vessel V. At least the first region 500A preferably is reinforced as discussed above to displace the stenosis 300 rather than being deformed into the vessel lumen by the stenosis. At least the first region 500A of the distal portion 500 has a smooth outside surface. The smooth surface is configured to prevent adherence of in vivo matter. The smooth surface is also well adapted to facilitate smooth non-traumatic explant by applying a force to the proximal end of the catheter 26A, 100'.

The catheter 26A, 100' is adapted to be cut through the braided structure, as discussed above, to size the catheter in-situ. The catheter 26A, 100' is advanced over a distal segment of the connector 30 until at least a portion of the braided structure 140 is positioned proximal of the retention feature, e.g., the barb(s) 244, 248.

Combination treatment can be provided by the method of FIG. 10 in that flow through the occluded region is improved and the stenosis 300 is treated to increase the patency of the vessel V downstream of the un-occluded zone A. The treatment of the stenosis 300 can be considered a distinct treatment. Also, the system 10A can provide access to blood that flows through the conduit 22. The access can be with a needle, e.g., to facilitate hemodialysis. Flow is mostly or entirely diverted through the system, as indicated the arrow entering the system 10A at the vessel end of the conduit 22 and the arrow exiting the distal end of the second region 500B. Upon removal of the system as applied in FIG. 10, the previously obstructed portion of the vessel V will be much more open than prior to the treatment.

The technique of FIG. 10 is primarily intended as a treatment for single vessel, e.g., with proximal and distal components coupled with segments of the same vessel. In some variations, adjoining venous or adjoining arterial vessels can be treated in this way.

A variant of the method of FIG. 10 involves connection of the system 10A from an artery to a vein. For example, a proximal end of the conduit 22 can be connected to a patient's brachial artery, e.g., by anastomosis. A distal end of the conduit 22 can be inserted into a vein and advanced to a position within the central venous system. In one method, a stenosis is observed in the central venous system and the distal end of the catheter 26, 100' is advanced distally until the outlet is distal of or at least unobstructed by the stenosis. Thereafter, blood is permitted to flow through the system 10A from the arterial vasculature to the venous vasculature beyond the stenosis. In this way, the presence of the stenosis does not interfere with dialysis treatment. As discussed herein, the catheter 26, 100' can be configured in at least that portion that interacts with the stenosis to displace the stenosis out of the lumen of the vessel. In some methods, the system 10A is left in place for a therapeutic period, e.g., at least as long as needed to improve patency through the stenosed region, and may thereafter be removed. A variety of techniques for connecting an arterial segment to a venous segment are discussed in the documents incorporated by reference hereinabove, such as (a) U.S. Pat. No. 6,102,884, see, e.g., FIG. 8; (b) Ser. No. 11/216,536 (US Publication No. 2006-0064159 A1), see, e.g., FIGS. 23A-23F, 26, and 37A-37E; (c) Ser. No. 11/600,589 (US Publication No. 2007-0167901 A1), see, e.g., FIGS. 8A-9E; and (d).

One advantageous way of treating a vessel using the system 10A is to insert the catheter 26, 100' only as far as needed. For example, the insertion of the catheter 26, 100' can be limited to advancing the distal end thereof only to vascular locations beyond the stenosis 300. While in certain embodiments, the method involves insertion of the distal end into a heart chamber, such as the left atrium, in other embodiments the distal end is placed outside of the heart within the vasculature. Placement outside the heart simplifies the procedure in that there is no need for the system 10A to interact with the heart. Also, the procedure can be completed more quickly since the catheter 26, 100' need not be advanced as far. Another potential advantage is that by shortening the catheter 26, 100', the blood and body tissues are exposed to less foreign material because the catheter can be shorter than if it were required to be advanced farther, e.g., into the heart.

FIG. 11 illustrates a class of treatments in which a bypass system 10B is applied to direct normal anatomical blood flow around the stenosis 300.

The bypass system 10B includes a catheter 604, a first connector 608, and a second connector 612. The catheter 604 has a proximal portion 616, a distal portion 620, and an elongate body 624 extending between the proximal and distal portions 616, 620. The catheter 604 can be similar to the catheter 100, for example providing a flow lumen for blood and sufficient structural support to maintain the lumen open when implanted beneath the skin. As discussed below, the catheter 604 is not intended to be inserted into the vasculature. So, features of the catheter 100 that facilitate such insertion can be omitted. Such feature may include radiopaque markers, as discussed above. In one variation the braided structure 140 in incorporated into the catheter 604.

The elongate body 624 defines an inner wall having an inner perimeter surrounding a blood flow lumen, similar to the lumen 120. The catheter 624 has a braided structure 140 embedded in the elongate body and disposed about the lumen. The first connector 608 is for fluidly coupling a first vascular graft 640 with the proximal portion 616 of the catheter 604. The first connector 608 comprises a connector body and an engagement feature. As discussed in connection with FIG. 4, the connector body of each of the connectors 608, 612 has an outer surface defining a first outer perimeter (e.g., diameter) and an inner surface defining a lumen. The engagement feature can be disposed on the outer surface of the connector body adjacent an end thereof. As discussed above, the engagement feature defines a second outer perimeter greater than the first outer perimeter.

The outer size of the catheter 604 is less critical than in other embodiments, but any of the sizes discussed above could be used. For example, the catheter 604 can an unconstrained size of anywhere form about 4 mm to about 8 mm. More generally, the outer diameter of the catheter 604 can be within a range of about 2 to about 14 mm. Larger sizes can be used as well since the catheter 604 is not required to fit inside a blood vessel in this application.

The proximal portion of the catheter 604 has a first configuration in a free state and a second configuration when in axial compression. In the first configuration, the inner perimeter is less than the first outer perimeter of the first connector 608. In the second configuration, the braided structure expands to permit the inner perimeter of the body of the catheter 604 to expand such that the proximal end portion of the catheter 604 can be advanced over the engagement feature of the connector body.

The second connector 612 can take any suitable form, but preferably is configured to securely engage a second vascular graft 644 with the distal portion of the catheter. For example, the second connector 612 can have a configuration similar to that of FIG. 4.

In one method, the first graft member 640 is coupled with a first vessel segment upstream of the stenosis 300. In this method both the proximal and distal ends of the catheter 604 are disposed outside the vasculature. The blood can flow into the graft member 640 through the proximal end of the graft 640. The second graft member 644 is coupled with a second vessel segment downstream of the stenosis 300. The first and second vessel segments can be portions of the same vessel in some applications. In other applications, the first and second vessel segments can be arterial vessels or venous vessels, which may be adjacent vessels or spaced apart by one or more intervening vessels.

A first end of the catheter 604 is coupled with the first graft member 640 by applying a connection force, e.g., providing relative motion between an end of the catheter 604 the connector 608 disposed on an end of the graft member 640. The second end of the catheter 604 can thereafter be coupled with the second graft member 644 in a similar fashion if the second connector 612 has similar constructions. When using these connectors, the braided structure 140 is expanded by the axial relative motion to permit the catheter 604 to be received over the corresponding connector. When the first and second grafts 640, 644 are connected to the catheter 604, a force required to disconnect the blood flow conduit from the first or second graft is significantly higher than the required connection force. The force required to disconnect is also greater than the expected forces to occur in the body. In some variations of this method, one or both of the first and second grafts 640, 644 at least a portion of the catheter 604 are disposed beneath the skin of the patient.

The system 10B can be applied with the first connector 608 disposed at an upstream location relative to the second connector 612, as illustrated in FIG. 11. In particular, the flow through the system 10B can be from the location of the arrow labeled "flow" in the figure. Blood then flows through the first graft 640 and into the catheter 604. The blood flows through a portion of the connector 608 to reach the catheter 604. Blood then flows from the catheter 604 into the second graft 644 by way of the connector 612 and into the vessel at the arrow distal of the second graft 644. In this way the vast majority of the blood flows into the vessel segment illustrated is bypassed around the stenosis 300. In other embodiments, the second connector 612 can be disposed at an upstream location relative to the first connector 608, which is the opposite of what is illustrated in FIG. 11.

In some variants of the system 10B of FIG. 11, the grafts 640, 644 can be pre-attached to a corresponding connector 608, 712 or can be separate components therefrom.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, it is contemplated that various aspects and features of the invention described can be practiced separately, combined together, or substituted for one another, and that a variety of combination and sub-combinations of the features and aspects can be made and still fall within the scope of the invention. Thus, it is intended that the scope of the present invention herein disclosed should not be limited by the particular disclosed embodiments described above, but should be determined only by a fair reading of the claims.

We claim:

1. A system for treating a stenosis, the system comprising:
an elongate body comprising a proximal portion, a distal portion, and a lumen extending therebetween along a longitudinal axis, wherein the distal portion configured to be inserted through a stenosis such that the proximal portion is positioned proximal of the stenosis and the distal portion is positioned distal of the stenosis;
an inner surface of the elongate body defining the lumen and an outer surface of the elongate body surrounding the inner surface;
a cuff coupled to an end portion of the elongate body and configured to be separated from the elongate body, wherein an outer surface of the cuff is configured to adhere to in vivo matter to stabilize the elongate body; and
a separation zone disposed between the cuff and the end portion of the elongate body, the separation zone comprising a separable bond between the elongate body and the cuff, wherein the cuff separates from the elongate body when a predetermined amount of force is applied to the separation zone without ripping the elongate body,
where the predetermined force is oriented in a longitudinal direction of the elongate body.

2. The system of claim 1, wherein the cuff comprises ePTFE.

3. The system of claim 1, wherein the cuff comprises a bioresorbable material.

4. The system of claim 1, wherein the cuff is bonded to the elongate body with an adhesive.

5. The system of claim 1, wherein the cuff comprises Dacron.

6. The system of claim 1, wherein the cuff is between 0.005 inches and 0.015 inches thick.

7. The system of claim 1, wherein the outer surface of the cuff comprises a shoulder, wherein the diameter of the shoulder is less than the diameter of the cuff.

8. The system of claim 7, wherein the shoulder is disposed within the lumen of the elongate body.

9. The system of claim 8, wherein the separation zone is restricted to the shoulder portion disposed within the lumen.

10. The system of claim 1, further comprising a tip portion disposed at a distal end of the elongate body, wherein the tip portion comprises a round atraumatic end.

* * * * *